US010849863B2

(12) United States Patent
States et al.

(10) Patent No.: US 10,849,863 B2
(45) Date of Patent: Dec. 1, 2020

(54) COMPOUNDS FOR TREATING CANCER, FOR ADMINISTERING, AND FOR PHARMACEUTICAL COMPOSITIONS

(75) Inventors: J. Christopher States, Goshen, KY (US); Ben Frazier Taylor, New Haven, CT (US); John O. Trent, Louisville, KY (US)

(73) Assignee: UNIVERSITY OF LOUISVILLE RESEARCH FOUNDATION, INC., Louisville, KY (US)

(*) Notice: Subject to any disclaimer, the term of this patent is extended or adjusted under 35 U.S.C. 154(b) by 15 days.

(21) Appl. No.: 14/114,352

(22) PCT Filed: Apr. 27, 2012

(86) PCT No.: PCT/US2012/035380
§ 371 (c)(1),
(2), (4) Date: Feb. 26, 2014

(87) PCT Pub. No.: WO2012/149266
PCT Pub. Date: Nov. 1, 2012

(65) Prior Publication Data
US 2014/0296242 A1  Oct. 2, 2014

Related U.S. Application Data

(60) Provisional application No. 61/479,939, filed on Apr. 28, 2011.

(51) Int. Cl.
*A61K 31/53* (2006.01)
*A61K 31/136* (2006.01)
*A61K 31/132* (2006.01)
*A61K 31/09* (2006.01)
*A61K 31/4439* (2006.01)
*A61K 31/135* (2006.01)
*A61K 31/138* (2006.01)
*A61K 31/495* (2006.01)
*A61P 35/00* (2006.01)

(52) U.S. Cl.
CPC ............ *A61K 31/135* (2013.01); *A61K 31/09* (2013.01); *A61K 31/132* (2013.01); *A61K 31/136* (2013.01); *A61K 31/138* (2013.01); *A61K 31/4439* (2013.01); *A61K 31/495* (2013.01); *A61K 31/53* (2013.01); *A61P 35/00* (2018.01)

(58) Field of Classification Search
None
See application file for complete search history.

(56) References Cited

U.S. PATENT DOCUMENTS

| 4,258,062 A | 3/1981 | Jonas et al. | |
| 7,687,473 B2* | 3/2010 | McGuire | 514/42 |
| 2005/0136065 A1* | 6/2005 | Valiante, Jr. | A61K 31/12 424/184.1 |
| 2009/0226422 A1* | 9/2009 | Chaudhary | A01K 67/0271 424/130.1 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface).*
Jordan, V. C. (Nature Reviews: Drug Discovery, 2, 2003, 205-213).*
International Search Report, PCT/US12/35380, dated Jul. 27, 2012, 4 pp.
Written Opinion, PCT/US12/35380, dated Jul. 27, 2012, 5 pp.
Dabrowska et al., "Methotrexate-induced senescence in human adenocarcinoma cells is accompanied by induction of p21waf1/cip1 expression and lack of polyploidy" Cancer Letters (2009) vol. 284, pp. 95-101.
Jiang et al., "Advances in mitotic inhibitors for cancer treatment" Mini Rev. Med Chem (2006) vol. 6, pp. 885-895.
Kaprealian et al., "Skin Cancer" at pp. 3-25, Chapter 1 in Handbook of Evidence-Based Radiation Oncology, 2nd Edition, Edited by Hansen et al., (2010) Springer, New York, New York USA.
Kubicky et al., "Central Nervous System" at pp. 29-67, Chapter 2 in Handbook of Evidence-Based Radiation Oncology, 2nd Edition, Edited by Hansen et al., (2010) Springer, New York, New York USA.
Lindon C., "Control of mitotic exit and cytokinesis by the APC/C" Biochem Soc Trans (2008) vol. 36, pp. 405-410.
Ma et al., "Antiproliferative Activity Against MCF-7 Breast Cancer Cells by Diamino-Triazaspirodiene Antifolates" Chem Biol Drug Des (2009) vol. 74, pp. 322-326.
McNeely et al., "Exit from arsenite-induced mitotic arrest is p53 dependent" Environ Health Perspect (2006) vol. 114, pp. 1401-1406.
McNeely et al., "Sensitivity to sodium arsenite in human melanoma cells depends upon susceptibility to arsenite-induced mitotic arrest" Toxicol Appl Pharmacol (2008a) vol. 229, pp. 252-261.
McNeely et al., "Mitotic arrest-associated apoptosis induced by sodium aresenite in A375 melanoma cells is BUBR1-dependent" Toxicol Appl Pharmacol (2008b) vol. 231, pp. 61-67.
Porter et al., "Telomerase-immortalized human fibroblasts retain UV-induced mutagenesis and p53-mediated DNA damage responses" DNA Repair (2006) vol. 5, pp. 61-70.
PubChem compound CID 2174924 (accessed at http://pubchem.ncbi.nlm.nih.gov/summary.cgi?cid=2174924 on Jul. 13, 2012).

(Continued)

Primary Examiner — Kortney L. Klinkel
Assistant Examiner — William Y Lee
(74) Attorney, Agent, or Firm — ALGM LLP; Harry J. Guttman

(57) ABSTRACT

Some embodiments of this invention include methods for treating disease and methods for administering a compound of the invention. In some aspects of the invention, diseases can be treated by administration of compositions comprising a compound of the invention. Pharmaceutical compositions of some embodiments of the present invention comprise a compound of the invention.

29 Claims, 13 Drawing Sheets

Specification includes a Sequence Listing.

(56) References Cited

OTHER PUBLICATIONS

PubChem compound CID 2304261 (accessed at http://pubchem.ncbi.nlm.nih.gov/summary/summary.cgi?cid=2304261 on Jul. 13, 2012).

Schmidt et al., "Mitotic drug targets and the development of novel anti-mitotic anticancer drugs" Drug Resist Updat (2007) vol. 10, pp. 162-181.

States et al., "Arsenite disrupts mitosis and induces apoptosis in SV40-transformed human skin fibroblasts" Toxicol Appl Pharmacol (2002) vol. 180, pp. 83-91.

States et al., "Targeting the anaphase promoting complex/cyclosome to inhibit cell cycle and to induce apoptosis in tumor cells" Society of Toxicology (Mar. 2012) vol. 126, Issue 1, p. 442 (Abstract No. PS 2049).

Taylor et al., "p53 Suppression of arsenite-induced mitotic catastrophe is mediated by p21CIP1/WAF1" J Pharmacol Exp Ther (2006) vol. 318, pp. 142-151.

Taylor et al., "Arsenite-induced mitotic death involves stress response and is independent of tubulin polymerization" Toxicol Appl Pharmacol (2008) vol. 230, pp. 235-246.

Van De Weerdt et al., "Uncoupling Anaphase-Promoting Complex/Cyclosome Activity from Spindle Assembly Checkpoint Control by Deregulating Polo-Like Kinase 1" Molecular and Cellular Biology (2005) vol. 25, pp. 2031-2044.

* cited by examiner

SEQUENCE LISTING

```
<160> NUMBER OF SEQ ID NOS: 1

<210> SEQ ID NO 1
<211> LENGTH: 311
<212> TYPE: PRT
<213> ORGANISM: Artificial Sequence
<220> FEATURE:
<223> OTHER INFORMATION: Eukaryotic

<400> SEQUENCE: 1

Lys Asp Leu Phe Ile Asn Glu Tyr Arg Ser Leu Leu Ala Asp Arg Leu
1               5                   10                  15

Leu His Gln Phe Ser Phe Ser Pro Glu Arg Glu Ile Arg Asn Val Glu
            20                  25                  30

Leu Leu Lys Leu Arg Phe Gly Glu Ala Pro Met His Phe Cys Glu Val
        35                  40                  45

Met Leu Lys Asp Met Ala Asp Ser Arg Arg Ile Asn Ala Asn Ile Arg
    50                  55                  60

Glu Glu Asp Glu Lys Arg Pro Ala Glu Glu Gln Pro Pro Phe Gly Val
65                  70                  75                  80

Tyr Ala Val Ile Leu Ser Ser Glu Phe Trp Pro Pro Phe Lys Asp Glu
                85                  90                  95

Lys Leu Glu Val Pro Glu Asp Ile Arg Ala Ala Leu Glu Ala Tyr Cys
            100                 105                 110

Lys Lys Tyr Glu Gln Leu Lys Ala Met Arg Thr Leu Ser Trp Lys His
        115                 120                 125

Thr Leu Gly Leu Val Thr Met Asp Val Glu Leu Ala Asp Arg Thr Leu
    130                 135                 140

Ser Val Ala Val Thr Pro Val Gln Ala Val Ile Leu Leu Tyr Phe Gln
145                 150                 155                 160

Asp Gln Ala Ser Trp Thr Leu Glu Glu Leu Ser Lys Ala Val Lys Met
                165                 170                 175

Pro Val Ala Leu Leu Arg Arg Arg Met Ser Val Trp Leu Gln Gln Gly
            180                 185                 190

Val Leu Arg Glu Glu Pro Pro Gly Thr Phe Ser Val Ile Glu Glu Glu
        195                 200                 205

Arg Pro Gln Asp Arg Asp Asn Met Val Leu Ile Asp Ser Asp Asp Glu
    210                 215                 220

Ser Asp Ser Gly Met Ala Ser Gln Ala Asp Gln Lys Glu Glu Glu Leu
225                 230                 235                 240

Leu Leu Phe Trp Thr Tyr Ile Gln Ala Met Leu Thr Asn Leu Glu Ser
                245                 250                 255

Leu Ser Leu Asp Arg Ile Tyr Asn Met Leu Arg Met Phe Val Val Thr
            260                 265                 270

Gly Pro Ala Leu Ala Glu Ile Asp Leu Gln Glu Leu Gln Gly Tyr Leu
        275                 280                 285

Gln Lys Lys Val Arg Asp Gln Gln Leu Val Tyr Ser Ala Gly Val Tyr
    290                 295                 300

Arg Leu Pro Lys Asn Cys Ser
305                 310
```

COMPOUNDS FOR TREATING CANCER, FOR ADMINISTERING, AND FOR PHARMACEUTICAL COMPOSITIONS

CROSS-REFERENCE TO RELATED APPLICATIONS

This application is a National Stage Entry of International Application No. PCT/US2012/035380 filed Apr. 27, 2012, entitled "COMPOUNDS FOR TREATING CANCER, FOR ADMINISTERING, AND FOR PHARMACEUTICAL COMPOSITIONS" which is herein incorporated by reference in its entirety, which claims the benefit of U.S. Provisional Application No. 61/479,939, filed Apr. 28, 2011, entitled "COMPOUNDS FOR TREATING CANCER, FOR ADMINISTERING, AND FOR PHARMACEUTICAL COMPOSITIONS" which is herein incorporated by reference in its entirety.

GOVERNMENT RIGHTS

This invention was made with Government support under ES011314, ES014559, and ES013372 awarded by the National Institutes of Health. The Government has certain rights in this invention.

BACKGROUND

Cancer is, in part, characterized by uncontrolled cellular proliferation. Hence, compounds that disrupt cell division (e.g., mitosis) can be part of a cancer chemotherapy armament. For example, some current mitotic disruptors in clinical use, such as paclitaxel, appear to target microtubules and thus can disrupt mitotic spindle function. Indeed, prolonged mitotic disruption may cause cells to undergo apoptosis. However, some tumors develop resistance to microtubule disrupting drugs by inactivation of the spindle checkpoint. Spindle checkpoint sensing is active until chromosomes are attached to the spindle. Also, the anaphase promoting complex/cyclosome (APC/C) appears to regulate mitotic progression, such as the metaphase to anaphase transition and the exit from mitosis. The exit from mitosis can lead to licensing of the pre-replication complexes. This licensing can lead to the subsequent transition from G1 phase to S phase and replication of DNA during S phase of the cell cycle. DNA replication can result in cell replication and tumor growth.

Thus, there is a need to develop cancer treatments that include drugs that target mitotic progression but do not or only minimally interact with microtubules. Some embodiments of the present invention include compounds, compositions, and methods that can address this need by, for example, targeting mitotic progression, targeting the licensing of the pre-replication complex, or being part of a cancer treatment that could decrease the development of treatment resistance.

SUMMARY

Some embodiments of the invention include methods for treating a disease in an animal comprising administering a composition comprising a compound, to the animal, where the compound is selected from the group consisting of a compound of Formula (I), a compound of Formula (II), and a compound of Formula (III). Some possible embodiments encompassed by this aspect of the invention are recited in this paragraph; none are to be considered essential or required. The method for treatment can include identifying an animal with the disease. The disease can be cancer, such as a cancerous tumor, or a cancer selected from the group consisting of basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, uterine cancer, and leukemias. In some instances, the compound can induce mitotic arrest or induce mitotic catastrophe. In other embodiments, the compound can inhibit activity of APC/C or can inhibit licensing the pre-replication complexes. The animal can be a mammal, such as a human. The administering can be by an oral route or by a parenteral route. The composition can comprise a racemic mixture of the compound. The compound can be selected from the group consisting of I-3, I-8, I-10, and I-13. If the compound is selected from Formula (III),

can be

The compound can be selected from the group consisting of III-1 to III-16. The compound can be selected from the group consisting of III-2, III-4, III-6, III-8, III-10, III-12, III-14, and III-16.

Some embodiments of the invention include methods for administering a composition to a cell comprising administering the composition comprising a compound, to the cell, where the compound is selected from the group consisting of a compound of Formula (I), a compound of Formula (II), and a compound of Formula (III). Some possible embodiments encompassed by this aspect of the invention are recited in this paragraph; none are to be considered essential or required. The composition can comprise a racemic mixture of the compound. The compound can be selected from the group consisting of I-3, I-8, I-10, and I-13. If the compound is selected from Formula (III),

can be

The compound can be selected from the group consisting of III-1 to III-16. The compound can be selected from the group consisting of III-2, III-4, III-6, III-8, III-10, III-12, III-14, and III-16. In some instances, the compound can induce mitotic arrest or induce mitotic catastrophe. In other embodiments, the compound can inhibit activity of APC/C or can inhibit licensing the pre-replication complexes. In some instances, the cell is a mammalian cell, such as a human cell. In other embodiments, the cell is part of an organ or is from a multicellular organism. In still other embodiments, the cell can be an animal cell selected from the group consisting of Lewis lung carcinoma cells, B16F10 melanoma cells, TC-1 cervical carcinoma cells, HS27 cells, MCF7 cells, MDA-MB-231 cells, A549 cells, THP-1 cells, 300.19 cells, Hela cells, A375 cells, SK-MEL-28 cells, GM0637 cells, tGM24 cells, CHO cells, mouse cells, and African green monkey cells. The cell can be a transfected cell.

Some embodiments of the invention encompass a composition comprising a compound, wherein the composition is a pharmaceutical composition and the compound is selected from the group consisting of a compound of Formula (I), a compound of Formula (II), and a compound of Formula (III). Some possible embodiments encompassed by this aspect of the invention are recited in this paragraph; none are to be considered essential or required. The composition can comprise a racemic mixture of the compound. The compound can be selected from the group consisting of I-3, I-8, I-10, and I-13. If the compound is selected from Formula (III),

OH can be

OH.

The compound can be selected from the group consisting of III-1 to III-16. The compound can be selected from the group consisting of III-2, III-4, III-6, III-8, III-10, III-12, III-14, and III-16. In some instances, the compound can induce mitotic arrest or induce mitotic catastrophe. In other embodiments, the compound can inhibit activity of APC/C or can inhibit licensing the pre-replication complexes. In other embodiments, the compound is present in a therapeutically effective amount to treat a disease, such as in a therapeutically effective amount to treat cancer. In some instances, the composition comprises a formulary ingredient and/or pyrogen-free water.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
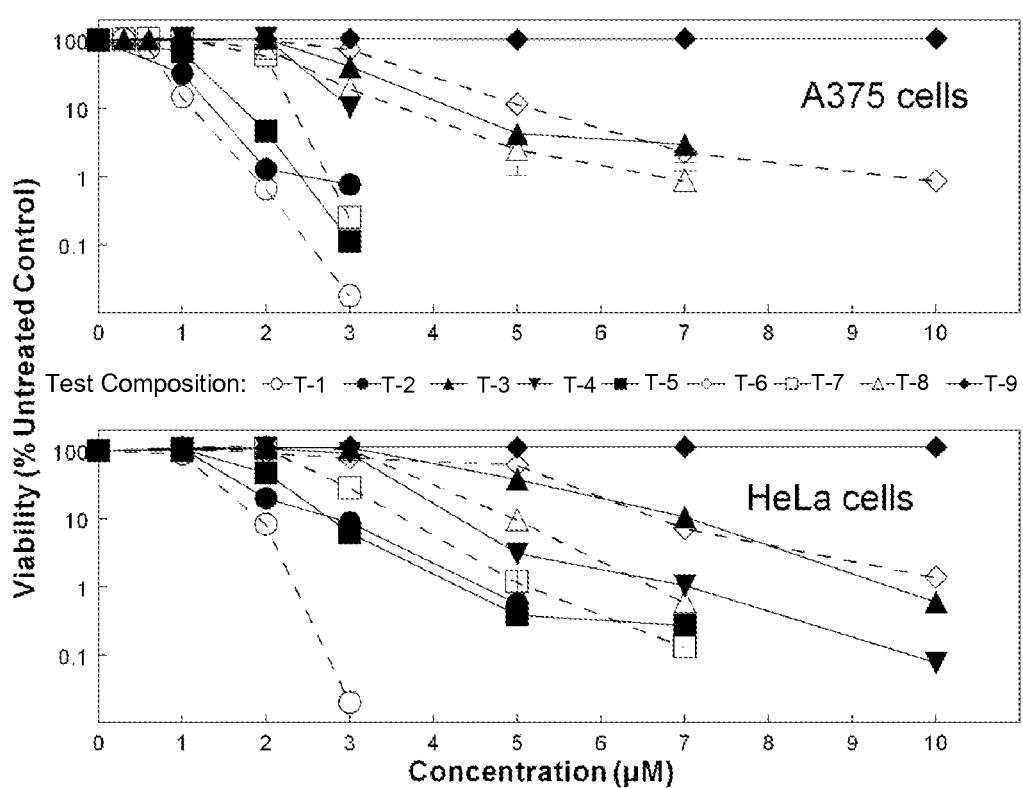
FIG. 1. Cytotoxicity induced in A375 cells (top) and HeLa cells (bottom) by T-1 to T-9. Data are truncated at the point at which the values were at or below control wells with no cells. Cells were exposed to the test compositions for 48 hours at time of assay.

Some embodiments of the invention include compounds of Formula (I), compounds of Formula (II), and compounds of Formula (III).

The disclosed compounds may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. Enantiomer means one of a pair of molecules that are mirror images of each other and are not superimposable. Diastereomers are stereoisomers that are not related as mirror images, most commonly because they contain two or more asymmetrically substituted carbon atoms, "R" and "S" represent the configuration of substituents around one or more chiral carbon atoms.

When the stereochemistry of the disclosed compounds is named or depicted by structure, the named or depicted stereoisomer is at least 60%, 70%, 80%, 90%, 99%, or 99.9% by weight pure relative to the other stereoisomers. When a single enantiomer is named or depicted by structure, the depicted or named enantiomer is at least 60%, 70%, 80%, 90%, 99%, or 99.9% optically pure. Percent optical purity by weight is the ratio of the weight of the enantiomer over the weight of the enantiomer plus the weight of its optical isomer When a disclosed compound is named or depicted by a structure without indicating the stereochemistry, and has at least one chiral center, it is to be understood that the name or structure encompasses one enantiomer of the compound free from the corresponding optical isomer, a racemic mixture of the compound, and mixtures enriched in one enantiomer relative to its corresponding optical isomer ("scalemic mixtures").

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer (s), and mixtures of diastereomeric pairs in which one diastereomeric pair is enriched relative to the other diastereomeric pair(s).

In some embodiments of the compounds of the invention, the compounds are chosen from Formula (I) and their stereoisomers:

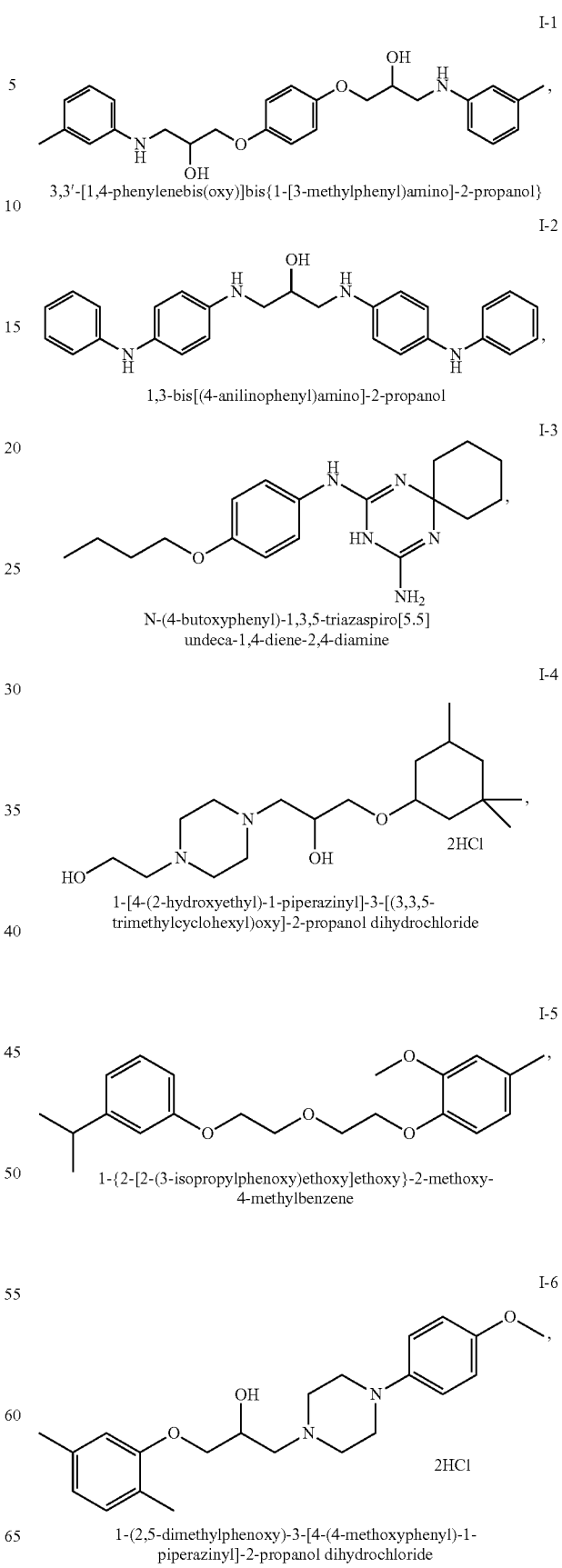

I-1
3,3'-[1,4-phenylenebis(oxy)]bis{1-[3-methylphenyl)amino]-2-propanol}

I-2
1,3-bis[(4-anilinophenyl)amino]-2-propanol

I-3
N-(4-butoxyphenyl)-1,3,5-triazaspiro[5.5] undeca-1,4-diene-2,4-diamine

I-4
1-[4-(2-hydroxyethyl)-1-piperazinyl]-3-[(3,3,5-trimethylcyclohexyl)oxy]-2-propanol dihydrochloride I-5
1-{2-[2-(3-isopropylphenoxy)ethoxy]ethoxy}-2-methoxy-4-methylbenzene I-6
1-(2,5-dimethylphenoxy)-3-[4-(4-methoxyphenyl)-1-piperazinyl]-2-propanol dihydrochloride

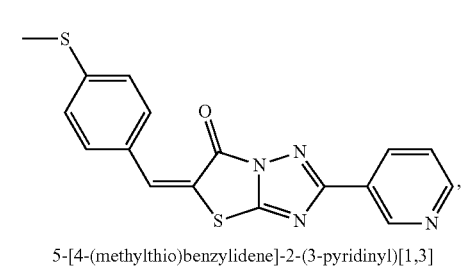

5-[4-(methylthio)benzylidene]-2-(3-pyridinyl)[1,3]
thiazolo[3,2-b][1,2,4]triazol-6(5H)-one

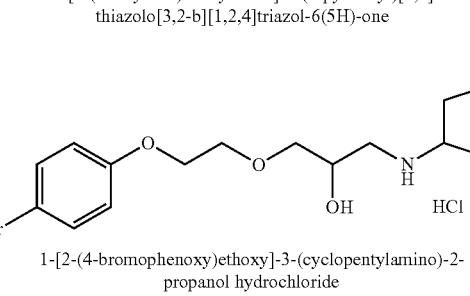

1-[2-(4-bromophenoxy)ethoxy]-3-(cyclopentylamino)-2-
propanol hydrochloride

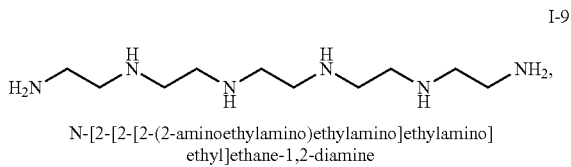

N-[2-[2-[2-(2-aminoethylamino)ethylamino]ethylamino]
ethyl]ethane-1,2-diamine

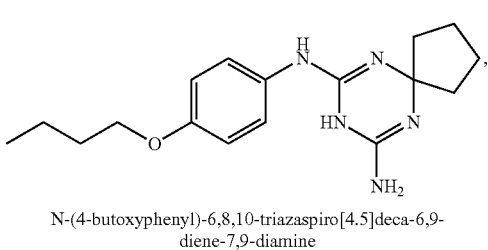

N-(4-butoxyphenyl)-6,8,10-triazaspiro[4.5]deca-6,9-
diene-7,9-diamine

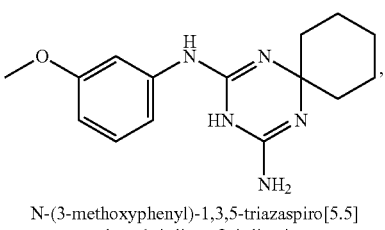

N-(3-methoxyphenyl)-1,3,5-triazaspiro[5.5]
undeca-1,4-diene-2,4-diamine

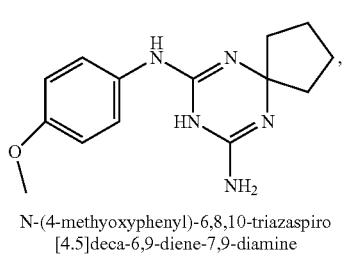

N-(4-methyoxyphenyl)-6,8,10-triazaspiro
[4.5]deca-6,9-diene-7,9-diamine

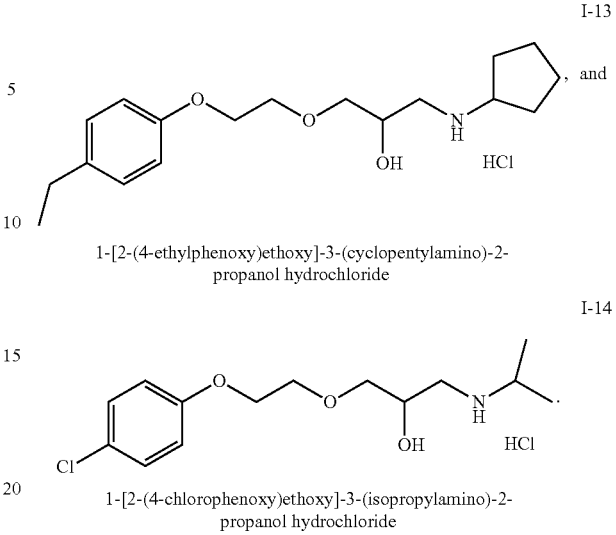

1-[2-(4-ethylphenoxy)ethoxy]-3-(cyclopentylamino)-2-
propanol hydrochloride

1-[2-(4-chlorophenoxy)ethoxy]-3-(isopropylamino)-2-
propanol hydrochloride

In some embodiments of the compounds of the invention, the compounds are chosen from Formula (II):

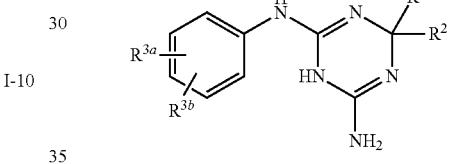

$R^1$ and $R^2$ can be the same or different, and can be H, halogen (e.g., F, Cl, Br, or I), hydroxyl, methoxy, ethoxy, propoxy, butoxy, pentoxy, hexoxy, methyl, ethyl, propyl, butyl, pentyl, hexyl, or heptyl. If the $R^1$, $R^2$ moieties create a chiral carbon at their attachment point, that chiral carbon can be in the (S) stereoisomer configuration or the (R) stereoisomer configuration. In some embodiments, $R^1$ and $R^2$ can bond to form a cycloalkyl, such as, but not limited to cyclopropyl, cyclobutyl, cyclopentyl, cyclohexyl, cycloheptyl, cyclooctyl, and cyclononyl. The carbons of the formed cycloalkyl can be replaced with one or more hetero atoms (e.g., one, two, three, four, or five heteroatoms), including, but not limited to, N, O, and S. $R^1$ and $R^2$ can be substituted or unsubstituted. $R^1$ and $R^2$ can be substituted or unsubstituted. The substitutions for $R^1$ and $R^2$ can include, but are not limited to hydroxyl, amine, amide, halogens (e.g., F, Cl, Br, or I), oxo, or nitro. The substitutions of $R^1$ and $R^2$ can include the fusion of a ring to the formed cycloalkyl or its hetero counterpart; such fused rings can be substituted or unsubstituted and can include but are not limited to fusions from cyclohexene, cyclohexadiene, benzene, cyclopentene, cyclopentadiene, furan, pyran, pyrrole, imidazole, pyrazole, pyridine, pyrazine, pyrimidine, or pyridazine. The substitutions of the fused ring can include, but are not limited to hydroxyl, amine, amide, halogens (e.g., F, Cl, Br, or I), oxo, or nitro. In some embodiments, the bivalent moiety attached to the $R^1$, $R^2$ carbon can be a lactam.

In some embodiments, the bivalent moiety attached to the $R^1$, $R^2$ carbon can be

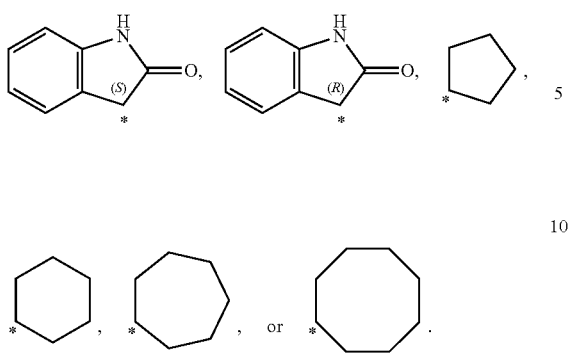

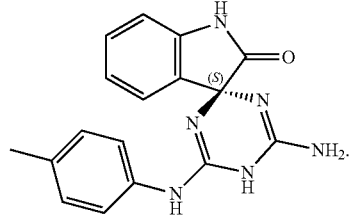

The asterisks indicate the carbons to which $R^1$ and $R^2$ are attached.

$R^{3a}$ and $R^{3b}$ can be the same or different and can be H, halogen (e.g., F, Cl, Br, or I), hydroxyl, methoxy, ethoxy, propoxy, butoxy, pentoxy, hexoxy, methyl, ethyl, propyl, butyl, pentyl, hexyl, or heptyl. $R^{3a}$ and $R^{3b}$ can be in the para, meta, or ortho position. $R^{3a}$ and $R^{3b}$ can be substituted or unsubstituted. The substitutions for $R^{3a}$ and $R^{3b}$ can include, but are not limited to hydroxyl, amine, amide, halogens (e.g., F, Cl, Br, or I), oxo, or nitro.

Some examples of Formula (II) include:

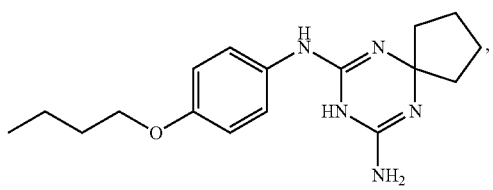

II-1

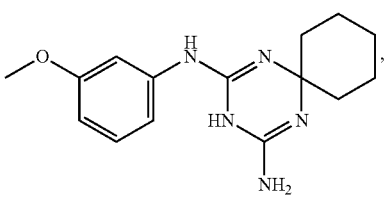

II-2

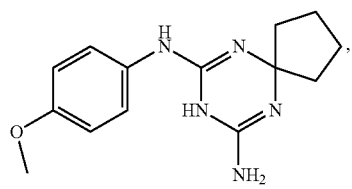

II-3

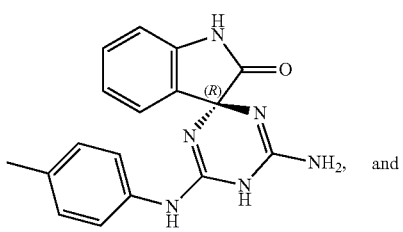

II-4 and

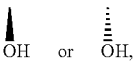

II-5

In some embodiments of the compounds of the invention, the compounds are chosen from Formula (III):

(III)

can be $\overset{|}{OH}$ or $\overset{\vdots}{OH}$, in that the attached chiral carbon can have an S configuration or an R configuration. $R^4$ can be H, halogen (e.g., F, Cl, Br, or I), hydroxyl, methoxy, ethoxy, methyl, ethyl, propyl, or butyl. $R^5$ and $R^6$ can be the same or different, and can be H, methyl, or ethyl. The alkyl groups for $R^4$, $R^5$, or $R^6$ can be substituted or unsubstituted. Substitutions can include, but are not limited to hydroxyl, amine, amide, halogens (e.g., F, Cl, Br, or I), or nitro.

$R^7$ can be a methyl, ethyl, propyl, or butyl, or a three-, four-, five-, six-, seven-, eight-, or nine-member ring that may include one or more heteroatoms in the ring. $R^7$ can be a substituted moiety or an unsubstituted moiety. Embodiments include one or multiple substitutions, for example, one, two, three, four, five, or six substitutions. Substitutions can include, but are not limited to alkoxy (e.g., methoxy, ethoxy, or propoxy), hydroxyl, amine, amide, halogens (e.g., F, Cl, Br, or I), nitro, alkyl (e.g., methyl, ethyl, or propyl), substituted alkyl (e.g., tri-halogenated methyl or trifluoromethyl). The rings can be conjugated, aromatic, unsaturated, or saturated. When the rings include heteroatoms, these heterocycles can have 1, 2, 3, or 4 heteroatoms (e.g., N, S, or O), which can be the same or different for a given ring. In some embodiments, $R^7$ is a substituted or an unsubstituted moiety selected from methyl, cyclopentyl, cyclohexyl, cyclooctyl, naphthyl, furyl, pyridyl, and pyrrolyl.

$X^-$ can be any suitable anion, such as an organic anion or an inorganic anion. Some inorganic anions include but are not limited to chloride, bromide, iodide, nitrate, sulfate, methyl sulfate, ethyl sulfate, or phosphate. Some organic anions include but are not limited to maleate, acetate, fumarate, or succinate. Of course, if $R^5$ and/or $R^6$ are hydrogen, and X is a halogen, then X can be part of a hydrogen halide salt (e.g., a hydrochloride salt).
Some examples of Formula (III) include:
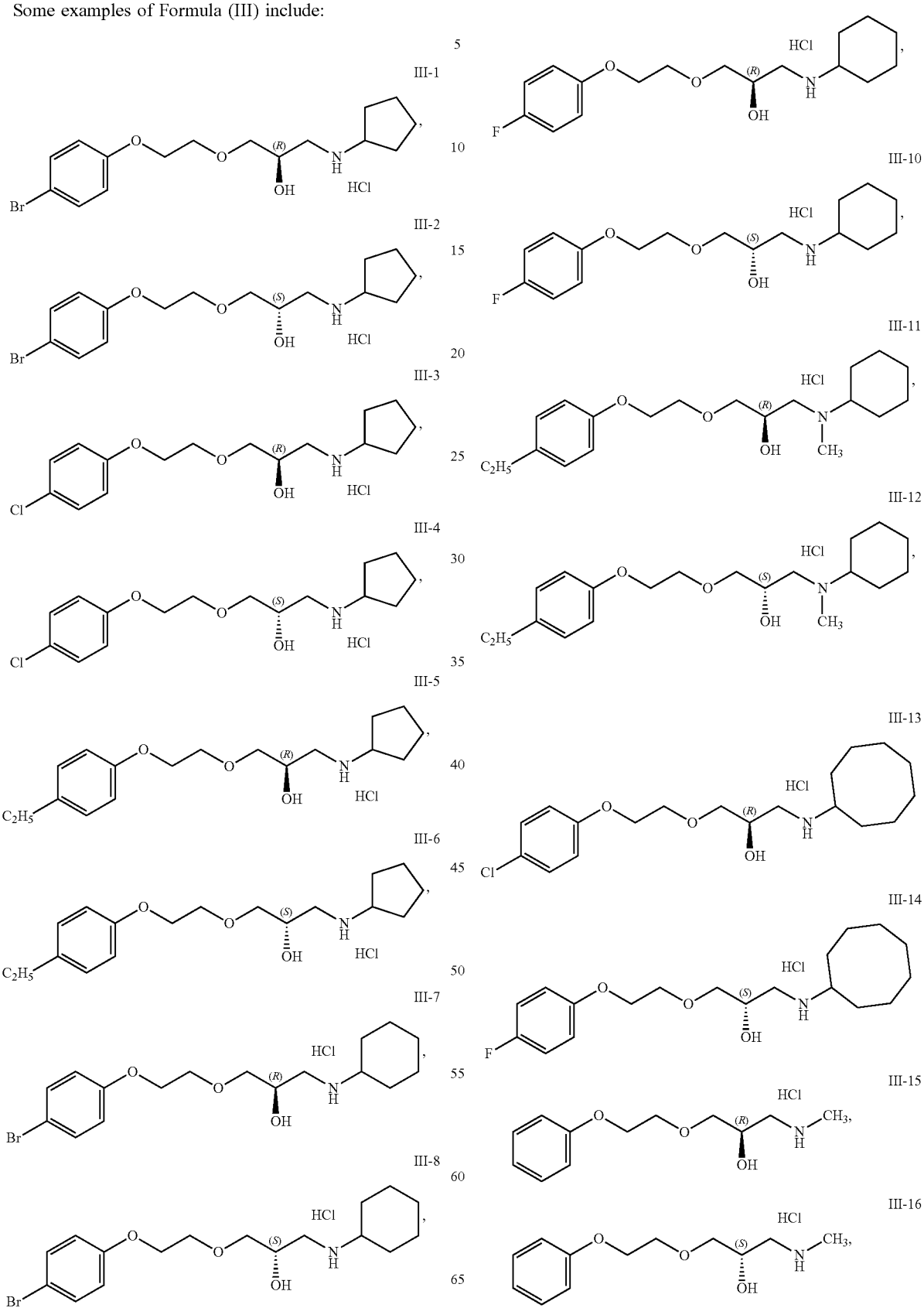

-continued

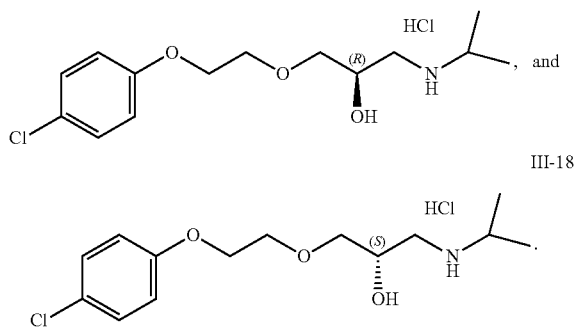

III-17

III-18 and

The compounds of the invention (e.g., any of the compounds of Formulas (I), (II), or (III)) can be in the form of salts, optical and geometric isomers, and salts of isomers. Also, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. For acidic compounds, salts can include metals, amines, or organic cations (e.g. quaternary ammonium). Furthermore, simple derivatives of the compounds (e.g., ethers, esters, or amides) which have desirable retention and release characteristics but which are easily hydrolyzed by body pH, enzymes, or other suitable means, can be employed.

Although some of the compounds have been identified by a particular virtual screening interface, any of the compounds of the invention could (but are not required to) interact with one or more parts of ANAPC2 or ANAPC11 that may result in modulation of activity, including but not limited to, inhibiting activity (e.g., decreasing, lessening, deactivating, or preventing) by direct interaction with one or more interfaces or inducing activity (e.g., increasing, stimulating, initiating, activating, or enhancing) by direct interaction with one or more interfaces. Modulation can also be indirect, such as, but not limited to, an allosteric effect on activity.

Some compounds of the invention can, but are not required to, modulate one or more of the following (1) mitotic progression, (2) activity of anaphase promoting complex/cyclosome, (3) activity of an E3 ubiquitin ligase complex, (4) cyclin B1 degradation, (5) securin degradation, (6) cyclin dependent kinase 1 activity, (7) entry into anaphase, (8) separase activity, (9) cleavage of cohesins, (10) chromatid separation, (11) mitotic arrest, (12) centrosome fragmentation, (13) programmed cell death (e.g., apoptosis), (14) mitotic catastrophe, (15) spindle checkpoint activation, (16) spindle checkpoint sensing, (17) exit from mitosis, (18) licensing the pre-replication complexes, (19) M-phase progression, (20) G1 to S phase transition, (21) mitotic arrest and apoptosis in paclitaxel-sensitive human carcinoma (e.g., cervical) cells, (22) cell cycle arrest and apoptosis in paclitaxel-resistant human carcinoma (e.g., melanoma) cells, (23) mitotic spindle function, (24) pause in mitosis, (25) targeting of cyclin B1, securin, and other mitotic proteins for degradation, (26) targeting of cyclin B1, securin, and other mitotic proteins, (27) stabilization of cyclin B1, (28) stabilization of securin, (29) activity of APC/C during M/G1 transition, (30) disruption of cell cycle regulation, (31) DNA replication, or (32) cell division.

Some compounds of the invention can, but are not required to, modulate one or more of the following (1) mitotic progression, (2) activity of anaphase promoting complex/cyclosome, (3) activity of an E3 ubiquitin ligase complex, (4) mitotic arrest, (5) centrosome fragmentation, (6) mitotic catastrophe, (7) exit from mitosis, (8) licensing the pre-replication complexes, (9) M-phase progression, (10) G1 to S phase transition, (11) mitotic arrest and apoptosis in paclitaxel-sensitive human carcinoma (e.g., cervical) cells, (12) cell cycle arrest and apoptosis in paclitaxel-resistant human carcinoma (e.g., melanoma) cells, (13) activity of APC/C during M/G1 transition, (14) disruption of cell cycle regulation, (15) DNA replication, or (16) cell division.

Some compounds of the invention can, but are not required to, modulate, as indicated, one or more of the following (1) inhibiting anaphase promoting complex/cyclosome, (2) inducing mitotic catastrophe, (3) inhibiting licensing the pre-replication complexes, (4) inducing cell cycle arrest and apoptosis in paclitaxel-resistant human carcinoma (e.g., melanoma) cells, (5) inhibiting DNA replication, or (6) inhibiting cell division.

Also, some compounds of the invention can bind to the amino acid side chains of ANAPC2 using at least a central bivalent or trivalent portion of a compound recited herein (e.g., —OC$_2$H$_4$OCH$_2$CH(OH)CH$_2$N(R$_2$)(R$_3$)— or

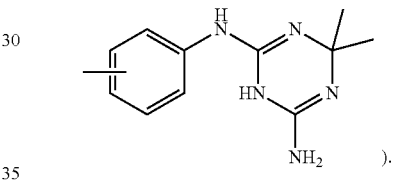

).

In some instances, modulation can include induction of mitotic arrest and apoptosis in paclitaxel-sensitive human carcinoma (e.g., cervical) cells, induction of cell cycle arrest and apoptosis in paclitaxel-resistant human carcinoma (e.g., melanoma) cells, or both.

In some instances, the treatment can be effective against cancers resistant to paclitaxel. In some instances, the affects can occur in normal cells, in cancer cells, in cancer cells that are paclitaxel sensitive, or in cancer cells that are paclitaxel resistant. In some instances, the treatment can result in changes in the morphology of apoptotic cells including, but not limited to, membrane "boiling" and cytoplasmic membrane blebs.

Some embodiments of the invention include compounds that can induce mitotic catastrophe index of at least about 1%, at least about 3%, at least about 5%, or at least about 10%. Some embodiments of the invention include compounds that can induce a mitotic index of at least about 5%, at least about 10%, at least about 15%, at least about 20%, or at least about 25%.

Some embodiments of the invention include administration of at least one compound of the invention to a cell. The cell can be a unicellular organism, or can be obtained from a multicellular organism, e.g., isolated cells from a multicellular host. The cell can be one of many cells treated. The cell can be a eukaryotic cell which can include but is not limited to fungi, yeast, insect cells (e.g., *Spodoptera frugiperda* (SF9)), animal cells such as CHO and mouse cells (e.g., Lewis lung carcinoma cells, B16F10 melanoma cells, and TC-1 cervical carcinoma cells), African green monkey cells (such as COS 1, COS 7, BSC 1, BSC 40, and BMT 10), and human cells (e.g., human carcinoma cells, A375 cells, HeLa cells, SK-MEL-28 cells, tGM24 cells, GM0637 cells, HS27 cells, MCF7 cells, MDA-MB-231 cells, A549 cells, THP-1 cells, and 300.19 cells), as well as plant cells. Of course, the cell may be transfected with one or more genes.

The compounds of the invention can be administered to animals by any number of administration routes or formulations. The compounds of the invention can also be used to treat animals for a variety of diseases. Animals include but are not limited to canine, bovine, porcine, avian, mammalian, and human.

Diseases that can be treated using the compounds of the invention include, but are not limited to cancers (such as cancerous tumors). Cancers that can be treated include, but are not limited to, basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, the lymph node, bone marrow, liver tissues, uterine cancer, and leukemias.

The route of administration of the compounds of the invention may be of any suitable route such as that which provides a concentration in the blood corresponding to a therapeutic concentration. Administration routes that can be used, but are not limited to the oral route, the parenteral route, the cutaneous route, the nasal route, the rectal route, the vaginal route. and the ocular route. The choice of administration route can depend on the compound identity, such as the physical and chemical properties of the compound, as well as the age and weight of the animal, the particular disease, and the severity of the disease. Of course, combinations of administration routes can be administered, as desired.

One or more compounds of the invention can be part of a composition and can be in an amount (by weight of the total composition) of at least about 0.001%, at least about 1%, at least about 10%, at least about 25%, at least about 50%, no more than about 75%, no more than about 90%, no more than about 95%, no more than about 99%, or no more than about 99.99%.

One or more compounds of the invention can be part of a composition and can be in an amount of about 0.5 µM, about 1.0 µM, about 2.0 µM, about 5.0 µM, about 10.0 µM, about 20.0 µM, about 25.0 µM, about 30.0 µM, about 40.0 µM, about 50.0 µM, about 60.0 µM, about 70.0 µM, about 75.0 µM, about 80.0 µM, about 90.0 µM, about 100.0 µM, about 150.0 µM, about 200.0 µM, at least about 0.1 µM, at least about 1.0 µM, at least about 10.0 µM, at least about 25.0 µM, at least about 50.0 µM, no more than about 75.0 µM, no more than about 100.0 µM, no more than about 200.0 µM, no more than about 400.0 µM, from about 0.5 µM to about 400.0 µM, from about 1.0 µM to about 100.0 µM, or from about 2.0 µM to about 50.0 µM.

A composition comprising a compound of the invention can include, but is not limited to, a single stereoisomer of the compound, a racemic mixture of the compound, or a scalemic mixture of the compound.

When a composition comprises a compound with at least two chiral centers, it is to be understood that the composition can be, but is not limited to, a composition comprising a diastereomer free of other diastereomers, a composition comprising a pair of diastereomers free from other diastereomeric pairs, a composition comprising mixtures of diastereomers, mixtures of diastereomeric pairs, a composition comprising mixtures of diastereomers in which one diastereomer is enriched relative to the other diastereomer(s), or a composition comprising mixtures of diastereomeric pairs in which one diastereomeric pair is enriched relative to the other diastereomeric pair(s).

One or more compounds of the invention can be purified or isolated in an amount (by weight of the total composition) of at least about 0.001%, at least about 1%, at least about 10%, at least about 25%, at least about 50%, no more than about 75%, no more than about 90%, no more than about 95%, no more than about 99%, no more than about 99.99%, from about 1% to about 95%, from about 10% to about 90%, or from about 25% to about 75%.

In some embodiments, one or more compounds of the invention can be used as part of a pharmaceutical composition. "Pharmaceutical composition" means a composition suitable for use in the treatment of animals. In some instances, the pharmaceutical composition is non-toxic and does not cause additional side effects compared to the drug delivered. In some therapies which are toxic (e.g., some cancer therapies), a pharmaceutical composition can deliver an amount of drug (e.g., one or more of compounds from Formula (I), Formula (II), or Formula (III)) sufficient to kill or alter the diseased cells (e.g., cancer cells or tumor cells) and not kill (or alter to a lesser extent) the non-diseased cells; there may be side effects inherent to the drug (e.g., the drug may harm the patient or the drug may be toxic or harmful to some non-diseased cells in the patient).

"Therapeutically effective amount" means an amount effective to achieve a desired and/or beneficial effect. An effective amount can be administered in one or more administrations. For some purposes of this invention, a therapeutically effective amount is an amount appropriate to treat an indication such as cancer. By treating an indication is meant achieving any desirable effect, such as one or more of palliate, ameliorate, stabilize, reverse, slow, or delay disease progression, increase the quality of life, or to prolong life. Such achievement can be measured by any method known in the art, such as physical measurement of mitotic arrest, mitotic catastrophe, cell phenotype, monitoring of the level of cancerous antigens in blood serum, or measuring patient life.

One or more compounds of the invention can be part of a pharmaceutical composition and can be in an amount of at least about 0.001%, at least about 1%, at least about 10%, at least about 25%, at least about 50%, no more than about 75%, no more than about 90%, no more than about 95%, no more than about 99%, no more than about 99.99%, from about 1% to about 95%, from about 10% to about 90%, or from about 25% to about 75%. The pharmaceutical composition can be presented in a dosage form which is suitable for the topical, subcutaneous, intrathecal, intraperitoneal, oral, parenteral, rectal, cutaneous, nasal, vaginal, or ocular administration route. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

Pharmaceutical compositions can be formulated to release the active compound substantially immediately upon the administration or any substantially predetermined time or time after administration. Such formulations can include, for example, controlled release formulations such as various controlled release compositions and coatings.

Other formulations (e.g., formulations of a pharmaceutical composition) include those incorporating the drug (or control release formulation) into food, food stuffs, feed, or drink.

The methods of treating an organism will involve treatment with an amount of the compound of the invention that is effective to treat the disease, condition, or disorder that the organism has, or is suspected of having, or to bring about a desired physiological effect. In some embodiments, the amount of one of at least one compound of the invention is administered to mammals (e.g., humans) at a concentration of about 0.05 to about 15 mg/kg body weight, about 0.2 to about 10 mg/kg body weight, about 0.5 to about 7 mg/kg body weight, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage will be about 6.5 mg/kg human body weight. In some instances, a mouse can be administered a dosage of, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention can be administered in combination with one or more other therapeutic agents for a given disease, condition, or disorder.

EXAMPLES

In Silico Screening

The anaphase promoting complex/cyclosome (APC/C) is an E3 ubiquitin ligase complex and appears to regulate mitotic progression and sequentially targets some proteins for degradation. For example, the APC/C ubiquitinylates, cyclin B1 and securin, are targeted for degradation. Degradation of cyclin B1 inhibits cyclin dependent kinase 1 (CDK1) activity necessary for entry into anaphase and degradation of securin activates separase which then cleaves the cohesins allowing the chromatids to separate in anaphase. If these events do not occur, the cell may arrest in mitosis. Prolonged arrest at the metaphase-anaphase junction can lead to centrosome fragmentation (also sometimes referred to as centrosome amplification) which may cause a multi-polar spindle and may activate programmed cell death processes as the cell undergoes mitotic death ("mitotic catastrophe").

An in silico approach to identify candidate drugs that will interfere with ANAPC11 (a catalytic subunit of APC/C) binding to its partner ANAPC2. Structural models based on homologous subunits (Rbx1 and Cullin) of the Cul1-Rbx1-Skp1-F boxSkp2 SCF ubiquitin ligase complex (Protein Data Bank entry 1LDJ) were developed for ANAPC11 and ANAPC2. Using these model structures, two sites ("A" & "B") on ANAPC2 in the ANAPC11 binding groove were targeted for the in silico screen.

The two sites were based on the following sequence for ANAPC2 with the first residue being numbered 1:

(SEQ ID NO: 1)
KDLFINEYRSLLADRLLHQFSFSPEREIRNVELLKLRFGEAPMHFCEV

MLKDMADSRRINANIREEDEKRPAEEQPPFGVYAVILSSEFWPPFKDE

KLEVPEDIRAALEAYCKKYEQLKAMRTLSWKHTLGLVTMDVELADRTL

SVAVTPVQAVILLYFQDQASWTLEELSKAVKMPVALLRRRMSVWLQQG

VLREEPPGTFSVIEEERPQDRDNMVLIDSDDESDSGMASQADQKEEEL

LLFWTYIQAMLTNLESLSLDRIYNMLRMFVVTGPALAEIDLQELQGYL

QKKVRDQQLVYSAGVYRLPKNCS

The two sites targeted include the following residues:

For site A, the following residues were used in the modeling: LEU17, ASP52, ASP55, SER56, ILE59, TYR81, ALA82, VAL83, ILE84, LEU85, SER86, SER87, GLU88, PHE89, TRP90, PRO92, TYR111, TYR115, LEU118, LYS119, MET121, ARG122, THR123, LEU124, SER125, TRP126, LYS127, HIS128, LEU130, and GLY131.

For site B, the following residues were used in the modeling: LEU17, HIS18, GLN19, ARG64, PHE78, GLY79, VAL80, TYR81, ALA82, VAL83, ILE84, LEU85, SER86, PRO92, LEU98, VAL100, PRO101, ASP103, ILE104, ALA107, LEU108, TYR111, CYS112, LEU124, SER125, TRP126, LYS127, HIS128, THR129, LEU130, GLY131, LEU132, VAL133, THR134, MET135, ASP136, SER145, VAL146, THR149, PRO150, ALA153, and VAL154.

The preliminary virtual screen targeting the ANAPC2:ANAPC11 interface on ANAPC2 used SurflexDock and the ZINC drug like library containing 3,300,000 compounds. The virtual screen was run on the Dataseam Grid (<<ky-dataseam.com>>). The compounds were scored using the native SurflexDock algorithm and the top 60 compounds were selected for each site. Five compounds were purchased from the site A list and four compounds were purchased from the site B list and subjected to further tests. The nine compounds are compounds I-1 to I-9.

Test Compositions and Cell Lines

Table 1 identifies the test compositions used in the experiments disclosed herein. The table also provides the targeting site that identified the compound (where appropriate), the stereoisomer identified by the virtual screen (where appropriate), and the source from which the test composition was purchased. The concentration of a test composition is the sum of the concentrations of all stereoisomers in that test composition.

TABLE 1

| Test Composition | In Silico Site | Compounds in the Test Composition | Source of Test Composition |
|---|---|---|---|
| T-1 | B (S,S) | A mixture of diastereomeric pairs of compound I-1 | ChemBridge Corp. of San Diego, CA (ID # 5271097) |
| T-2 | B (S) | A racemic mixture of compound I-2 | ChemBridge Corp. of San Diego, CA (ID # 5467512) |
| T-3 | B | Compound I-3 | ChemBridge Corp. of San Diego, CA (via <<hit2lead.com>>; ID # 6071473) |
| T-4 | B (S) | A racemic mixture of compound I-4 | ChemBridge Corp. of San Diego, CA (ID # 6265880) |
| T-5 | A | Compound I-5 | ChemBridge Corp. of San Diego, CA (ID #6481394) |
| T-6 | A (S) | A racemic mixture of compound I-6 | ChemBridge Corp. of San Diego, CA (ID # 6945608) |
| T-7 | A | Compound I-7 | ChemBridge Corp. of San Diego, CA (ID # 7366564) |
| T-8 | A (S) | A racemic mixture of compound I-8 | ChemBridge Corp. of San Diego, CA (via <<hit2lead.com>>; ID #7939338) |
| T-9 | A | Compound I-9 | Acros Organic of New Jersey, USA (Catalog #32029-0050) |
| T-10 | Analog | Compound I-10 | ChemBridge Corp. of San Diego, CA (via <<hit2lead.com>>; ID # 6067889) |
| T-11 | Analog | Compound I-11 | ChemBridge Corp. of San Diego, CA (via <<hit2lead.com>>; ID # 6074747) |
| T-12 | Analog | Compound I-12 | ChemBridge Corp. of San Diego, CA (via <<hit2lead.com>>; ID # 6068147) |
| T-13 | Analog | A racemic mixture of compound I-13 | ChemBridge Corp. of San Diego, CA (via <<hit2lead.com>>; ID # 7931840) |
| T-14 | Analog | A racemic mixture of compound I-14 | ChemBridge Corp. of San Diego, CA (via <<hit2lead.com>>; ID # 5367012) |

Table 2 identifies the cell lines with their sources used in the experiments disclosed herein.

TABLE 2

| Cell Line | Source of Cell Line |
|---|---|
| A375 | ATCC # CRL-1619 (human melanoma) |
| HeLa | ATCC # CRL-2 (human cervical carcinoma) |
| SK-MEL-28 | ATCC # HTB-72 (human melanoma) |
| GM0637 | NIGMS Human Mutant Cell Repository (SV40 transformed and immortalized human skin fibroblasts) |
| tGM24 | Derived from GM00024 normal diploid human skin fibroblasts obtained from NIGMS Human Mutant Cell Repository and transduced with human telomerase (hTERT). Derivation described in Porter et al., DNA Repair, Vol. 5, No. 1, pages 61-70 (Jan. 5, 2006). |

Viability Assays Using AlamaBlue

The test compositions in Table 1 were tested first for their ability to induce cytotoxicity in dose response curves using an AlamarBlue assay using two cancer cell lines.

The method used for the viability assay follows. Cells were seeded in 96-well plates for measuring cell growth during treatment by the tested compound using the Alamar-Blue fluorescence assay (Biosource International, Inc., Camarillo, Calif.). AlamarBlue (resazurin) is a soluble, non-toxic dye used to monitor the functional electron transport chain of a viable cell by reduction of the dye from its oxidized, non-fluorescent (blue) state to the reduced, fluorescent (pink) state (resorufin). AlamarBlue was added six hours prior to the desired time point in an amount equal to 10% (v/v) of the culture volume, and the plates were returned to the incubator. At the end of the six hour incubation, the amount of AlamarBlue reduction was measured using a fluorometric plate reader (emission=535 nm; excitation=590 nm). The plate reader was blanked by reading the fluorescence of cell free medium supplemented with AlamarBlue (States et al., Toxicol. Appl. Pharmacol., Vol. 180, pages 83-91 (2002)). Data are reported as a percentage of the untreated control. Three independent experiments were analyzed and results are shown as average±standard deviation.

Clonogenic Viability Assays

Clonogenic assays are used to determine the impact of a test compositions on the ability of cells to replicate. Cells are plated at cloning densities (100 and 500 cells per well in a 6-well plate; 3 wells of each cell number), and allowed to attach and stabilize overnight. Cells are then treated in dose-response experiments with test composition(s) (one concentration of test composition per plate) and incubated for 7-10 days to allow colonies of >30 cells to form. Colonies are stained with crystal violet and counted. Colony forming ability is then calculated as a percent of control by setting the mean number of colonies per well of cells treated with vehicle (0.1% DMSO) equal to 100 percent.

Visual Assessment of Cytotoxicity

The cytotoxicity of the compounds were initially assessed visually and by photomicroscopy. Visual inspection of dose response experiments over a protracted time course provides valuable information on the responses of cells to the treatments. Phase contrast microscopy allows one to assess whether cells are undergoing mitotic arrest and/or apoptosis by their altered morphology. Mitotic cells rounded up with smooth membranes and often condensed chromosomes aligned at a metaphase plate were clearly visible. Apoptotic cells round up and the cellular membrane had a 'boiling' morphology. Cells were plated in 24-well plates and allowed to attach and stabilize overnight. Cells were then treated with compounds in dose response and photomicrographs were taken at various time points over 2 days. Photographs were assembled in composite figures showing dose response at a given time point.

Nuclear Morphology Index Determination

Figure 2:
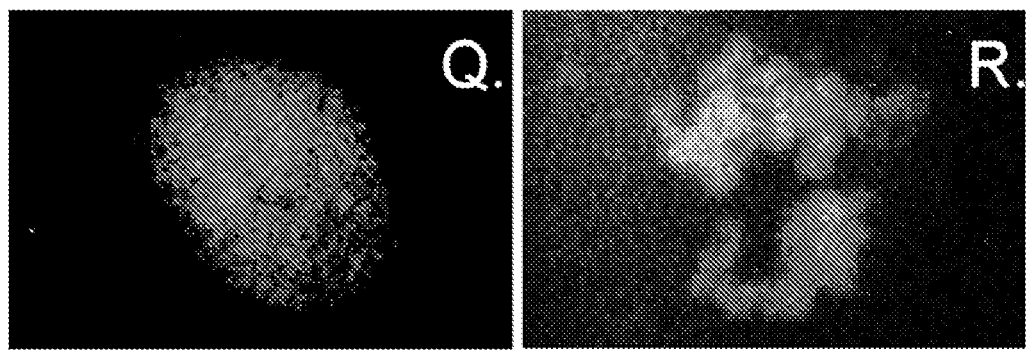
FIG. 2. Example pictures using DAPI stain from normal nuclei (Q), apoptotic nuclear fragmentation (R), mitotic spread (S), and mitotic catastrophe (T). Example pictures are from experiments reported in Taylor et al., J. Pharmacol. Exp. Ther., Vol. 318, pages 142-151 (2006).
Figure 2:
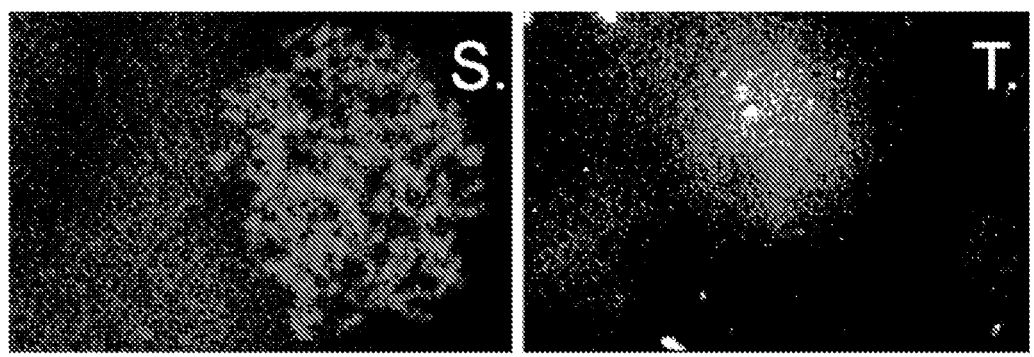

Cells were harvested for mitotic index analysis by trypsinization. Media, wash, and trypsinized cells were collected together and centrifuged to pellet all the cells. Cells were resuspended in 150 mL serum free media and 2.5 mL 0.4% KCl was added. The suspension was incubated for 10 minutes at 37° C. Methanol:acetic acid fixative solution (3:1, v/v) was then added to 2% (v/v) and cells were collected by centrifugation. Cells were resuspended in 2.5 mL fixative solution and fixed at room temperature for 20 minutes. Samples were centrifuged; pellets were resuspended in 0.5 mL fixative and chilled on ice for one hour. Aliquots of the suspensions were dropped onto slides (two slides per sample), air dried, and stained with Wright Giemsa solution (States et al., Toxicol. Appl. Pharmacol., Vol. 180, pages 83-91 (2002); Taylor et al., J. Pharmacol. Exp. Ther., Vol. 318, pages 142-151 (2006)). Slides were examined under a microscope and at least 200 cells were counted on each slide for determination of mitotic index and mitotic catastrophe index. Only cells with distinct interphase nuclei appearance (panel Q from FIG. 2), metaphase spread appearance (panel S from FIG. 2), or mitotic catastrophe appearance (panel T from FIG. 2) were counted. Mitotic index and mitotic catastrophe index were determined using the following formula:

Mitotic index=(cells with mitotic spread appearance as exemplified in panel $S$ of FIG. 2)/(total number of counted cells)

Mitotic catastrophe index=(cells with mitotic catastrophe appearance as exemplified in panel $T$ of FIG. 2)/(total number of counted cells)

Three independent experiments were analyzed. DAPI stain in mounting media (Molecular Probes) added directly to the slides was used to identify DNA in interphase nuclei, mitotic spreads, mitotic catastrophe, and nuclear fragmentation by fluorescence microscopy. See FIG. 2.

Test compositions T-1 to T-9 in Table 1 were tested for their ability to induce mitotic arrest using a mitotic spread assay because it can also be used to score for mitotic catastrophe (Taylor et al., J. Pharmacol. Exp. Ther., Vol. 318, Pages 142-151 (2006); Taylor et al., Toxicol. Appl. Pharmacol., Vol. 230, Pages 235-246 (2008)). Using the Alamar-Blue viability assays, FIG. 1 shows that test compositions T-1 to T-8 were cytotoxic to both cell lines in the low μM range (less than 10% viability at <10 nM). In these tests, a single concentration of each test composition was tested based on cytotoxicity results of FIG. 1 and on results of observational studies to determine the dose and time course of morphological changes induced (data not shown). The concentrations chosen were the minimum concentrations required to induce <10% survival and morphological changes at 16-24 hours.

Figure 3:
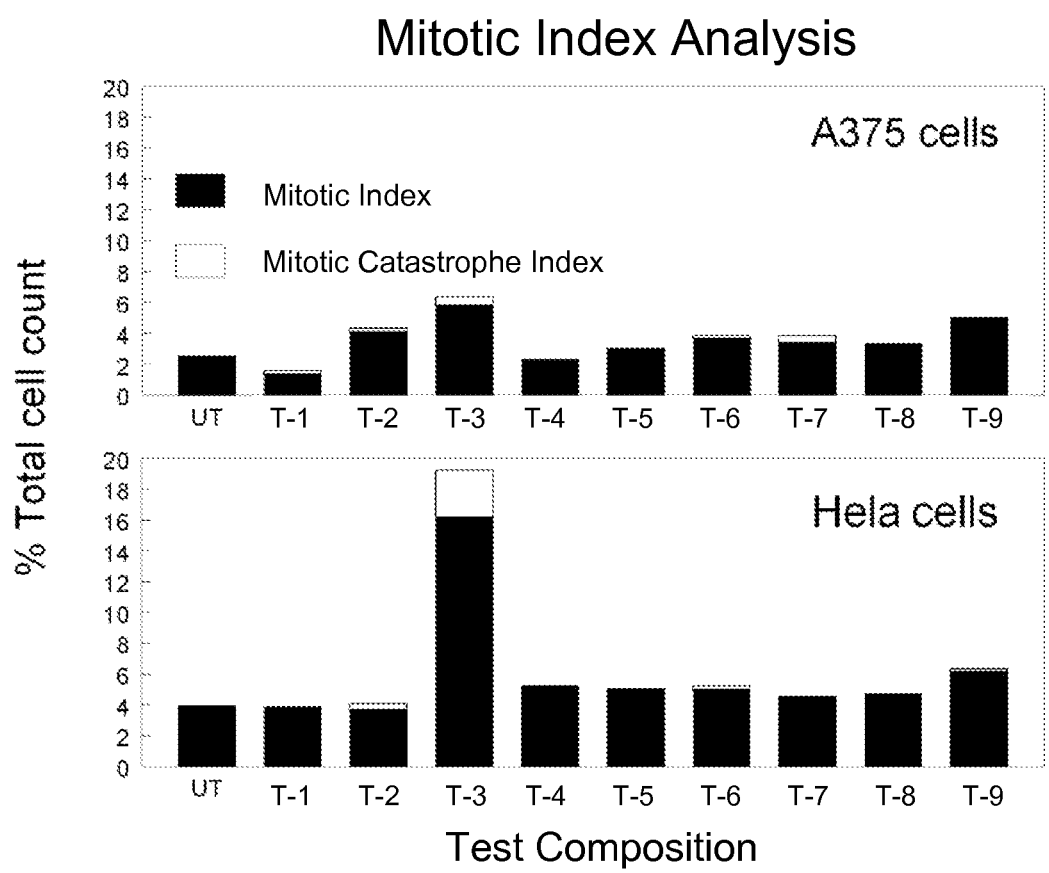
FIG. 3. Mitotic index and mitotic catastrophe index determination in A375 cells (top) and HeLa cells (bottom) treated with selected concentrations (1-10 µM) of T-1 to T-9 for eighteen hours. UT is untreated control.

The results (FIG. 3) of the mitotic index determinations indicate that T-3 induces the highest mitotic index in both A375 cells and HeLa cells. HeLa cells appeared more sensitive than A375 cells. In this experiment, HeLa cells were treated with twice the concentration used for A375 cells, so this difference in sensitivity may be dose dependent. T-3 is among the group ranked high for targeting Site A.

Figure 4:
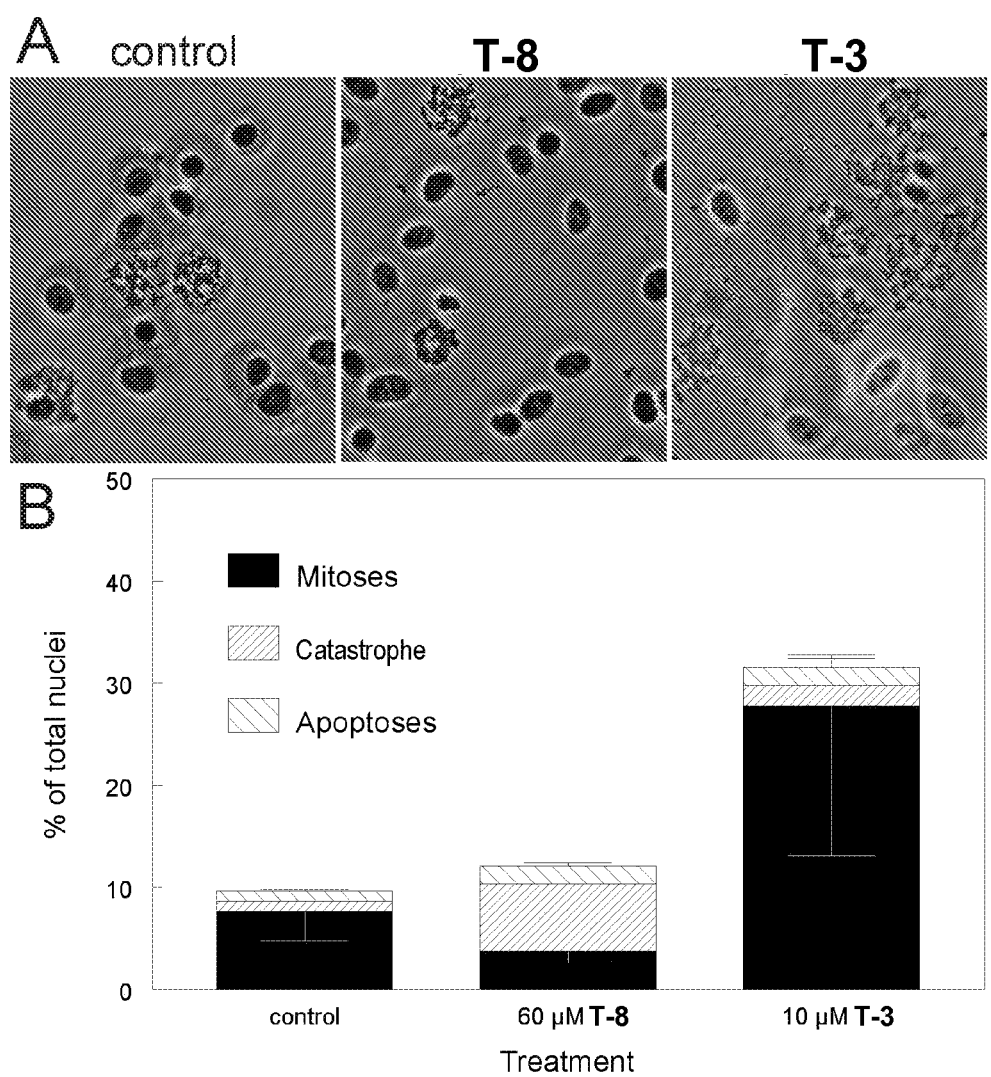
FIG. 4. Mitotic index determination. Hela cells were treated with 60 µM of T-8, 10 µM T-3, or DMSO (control) for 24 h. Slides were prepared for mitotic index and mitotic catastrophe determination. A. Photomicrographs of mitotic spreads. B. Quantitation of mitotic index and mitotic catastrophe.

FIG. 4 shows that the percent of nuclei present as clean mitotic spreads was increased in cells treated with T-3 and decreased in cells treated with T-8 (p<0.05). Both compositions induced a higher percentage of nuclei presenting as mitotic catastrophe (p<0.05).

Figure 5A:
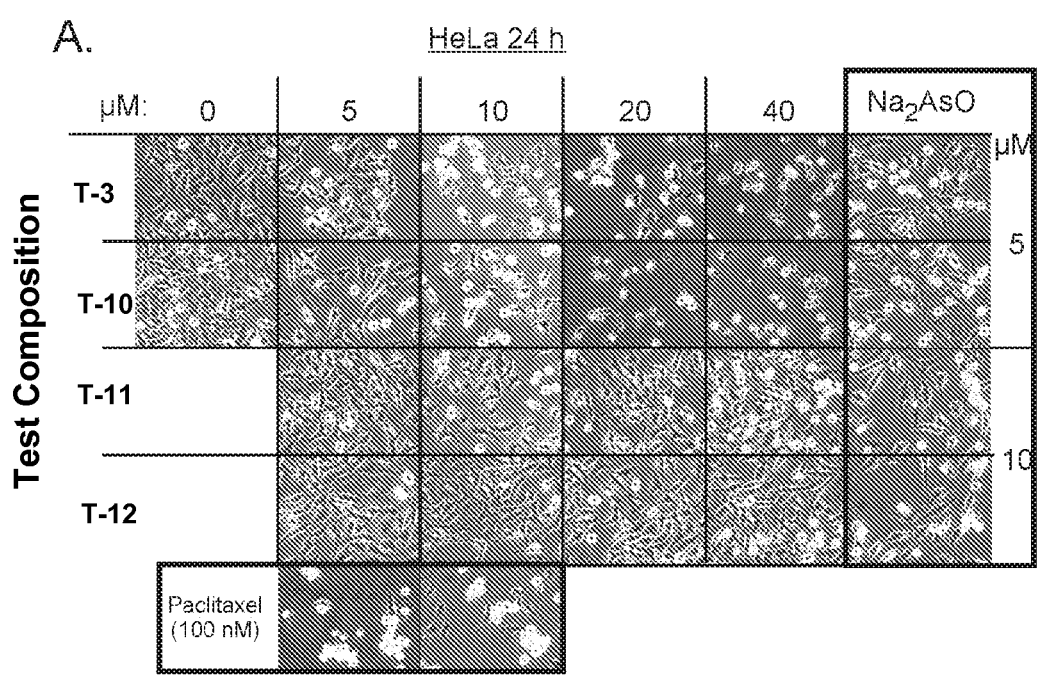
FIG. 5A. Visual assessment of toxicity of T-3, T-10, T-11, and T-12 on HeLa cells (paclitaxel sensitive) cells. Cells were plated in a 24-well plated and treated with indicated concentrations of the compounds for the times indicated. Cells were treated with paclitaxel and sodium arsenite as controls.
Figure 5B:
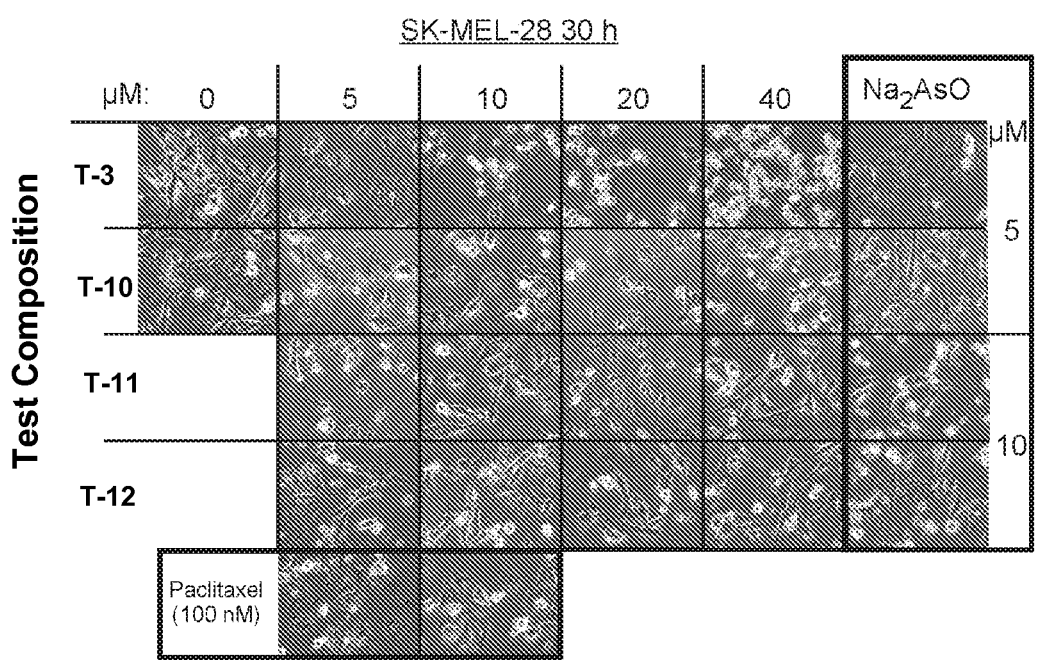
FIG. 5B. Visual assessment of toxicity of T-3, T-10, T-11, and T-12 on SK-MEL-28 cells (paclitaxel resistant) cells. Cells were plated in a 24-well plated and treated with indicated concentrations of the compounds for the times indicated. Cells were treated with paclitaxel and sodium arsenite as controls.

FIG. 5 shows that rounded up cells in mitosis accumulate in cells treated with T-3, and at slightly higher concentrations, with T-10. T-11 and T-12 appear to have less effect.

Figure 6A:
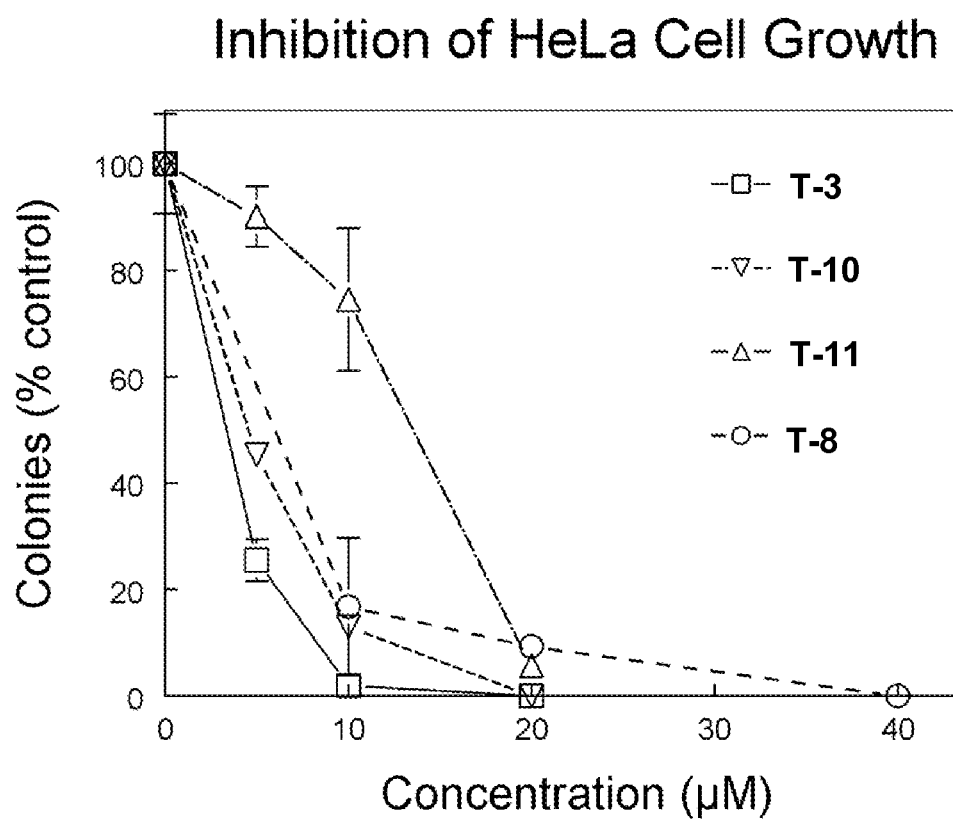
FIG. 6A. Hela cell (paclitaxel sensitive) cytotoxicity of T-3, T-8, T-10, and T-11 determined using clonogenic assays. Hela cells were seeded in 6-well plates at 500 cells per well and allowed to attach overnight. Cells were then exposed to the indicated concentrations of the test compounds delivered in DMSO (0.1% final concentration). Colonies were stained and counted after 10 days.
Figure 6B:
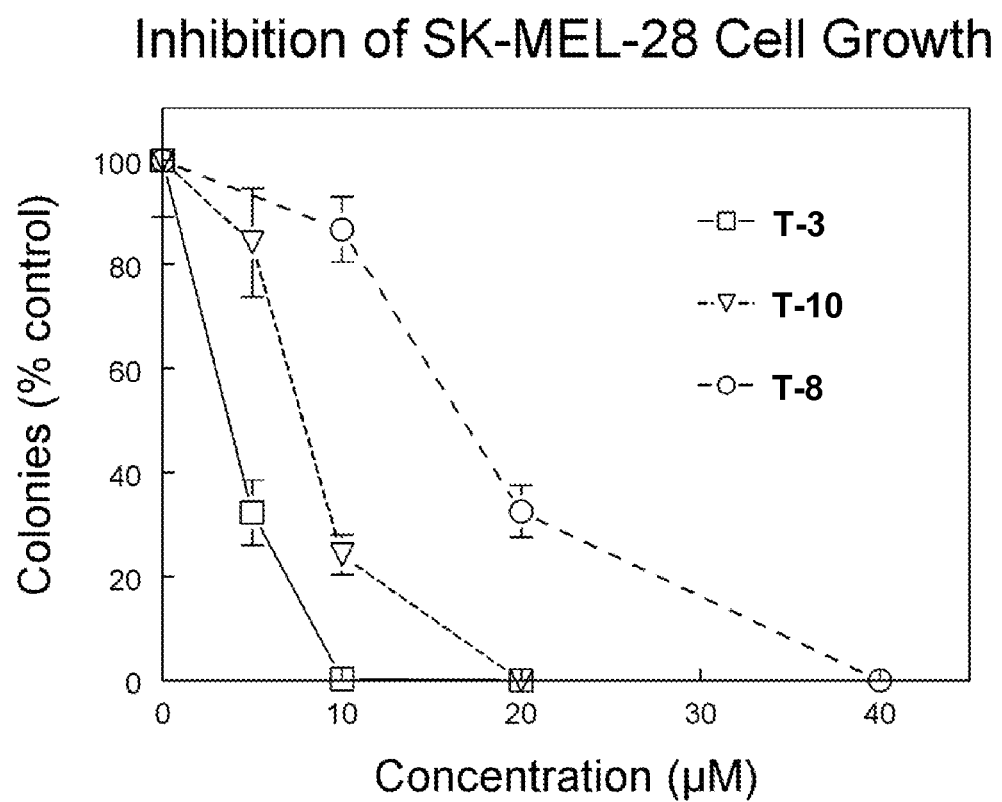
FIG. 6B. SK-MEL-28 cell (paclitaxel resistant) cytotoxicity of T-3, T-8, and T-10 determined using clonogenic assays. SK-MEL-28 cells were seeded in 6-well plates at 500 cells per well and allowed to attach overnight. Cells were then exposed to the indicated concentrations of the test compounds delivered in DMSO (0.1% final concentration). Colonies were stained and counted after 10 days.

FIG. 6A shows Hela cell (paclitaxel sensitive) cytotoxicity of T-3, T-8, T-10, and T-11 determined using clonogenic assays. All four tested compounds decreased colony formation. T-11 appeared least effective. FIG. 6B shows SK-MEL-28 (paclitaxel resistant) cytotoxicity of T-3, T-8, and T-10 determined using clonogenic assay. All three tested compositions decreased colony formation.

Figure 7:
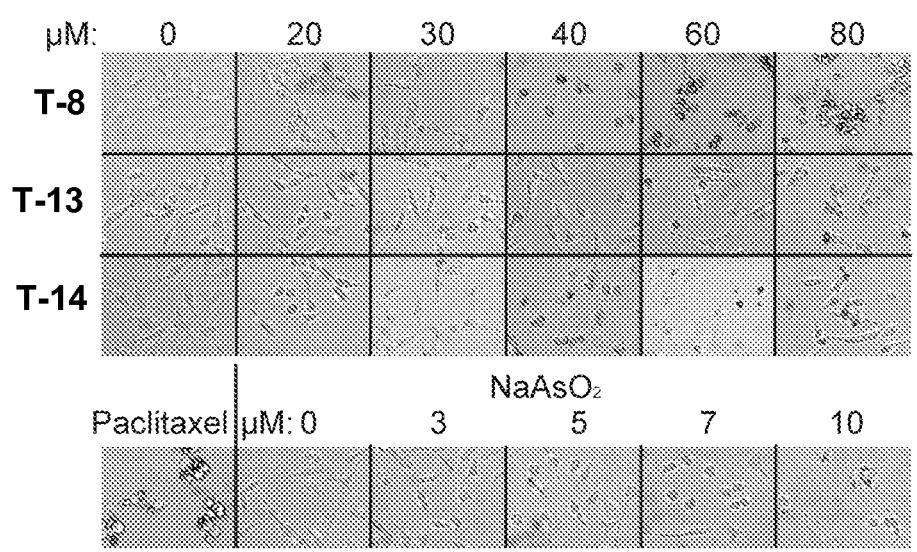
FIG. 7. Visual assessment of cytoxicity of T-8, T-13, and T-14 in HeLa cells. Photos from 24 well plate. 10×, 32 h incubation FIG. 8A. Cytoxicity of T-8, T-13, and T-14 in HeLa cells using the Alamar Blue assay. Cells were seeded in 96-well plates and treated with indicated concentrations of test compositions for 32 h. Alamar Blue was added during the final 6 h of incubation and fluorescence was read on a plate reader. All values were corrected by the average of the blank (media only) wells, then normalized to the DMSO "zero" controls. A polynomial line of best fit has been included for each data set.

FIG. 7 provides a visual assessment of cytotoxicity of T-8, T-13, and T-14 in HeLa cells. The rounded up cells with medial lines represent metaphase cells; some anaphase cells can also be seen. Cells with membrane blebbing that appeared to be "boiling" or fuzzy are representative of apoptotic cells. Shrunken cells with pyknosis/nuclear fragmentation represent cells that were further along in the apoptotic process.

Figure 8A:
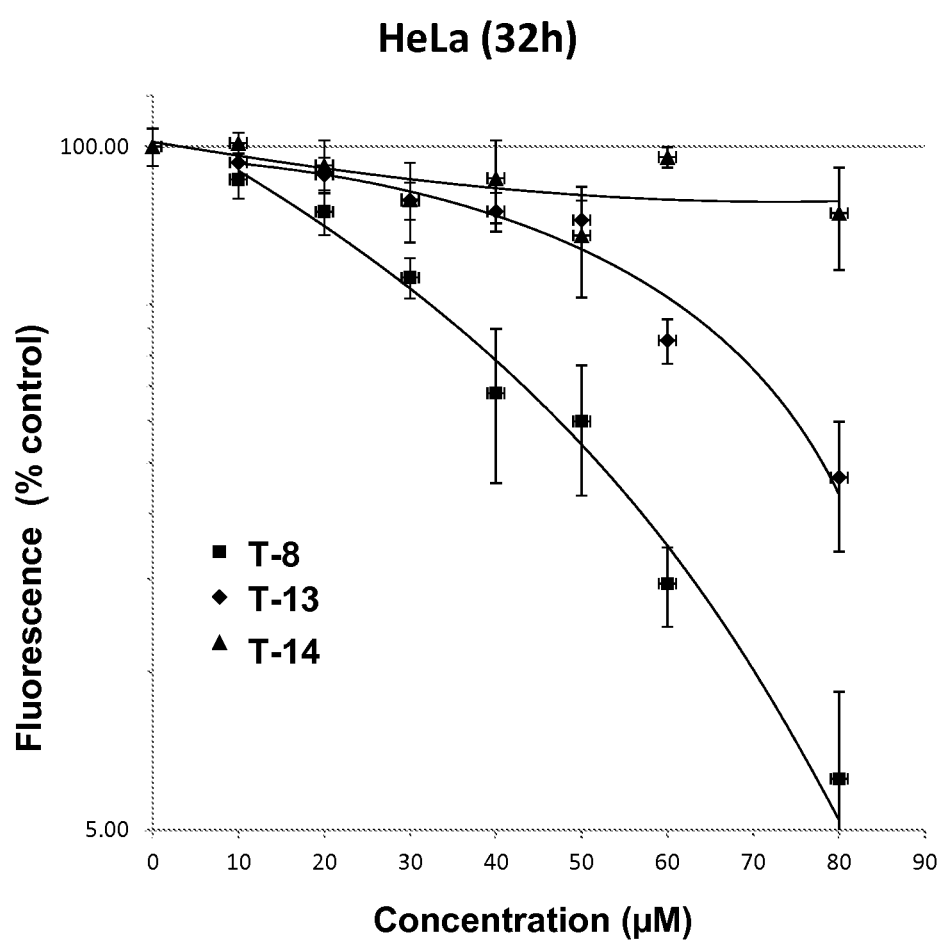
FIG. 8B. Cytoxicity of T-8, T-13, and T-14 in A375 cells using the Alamar Blue assay. Cells were seeded in 96-well plates and treated with indicated concentrations of test compositions for 32 h. Alamar Blue was added during the final 6 h of incubation and fluorescence was read on a plate reader. All values were corrected by the average of the blank (media only) wells, then normalized to the DMSO "zero" controls. A polynomial line of best fit has been included for each data set.
Figure 8B:
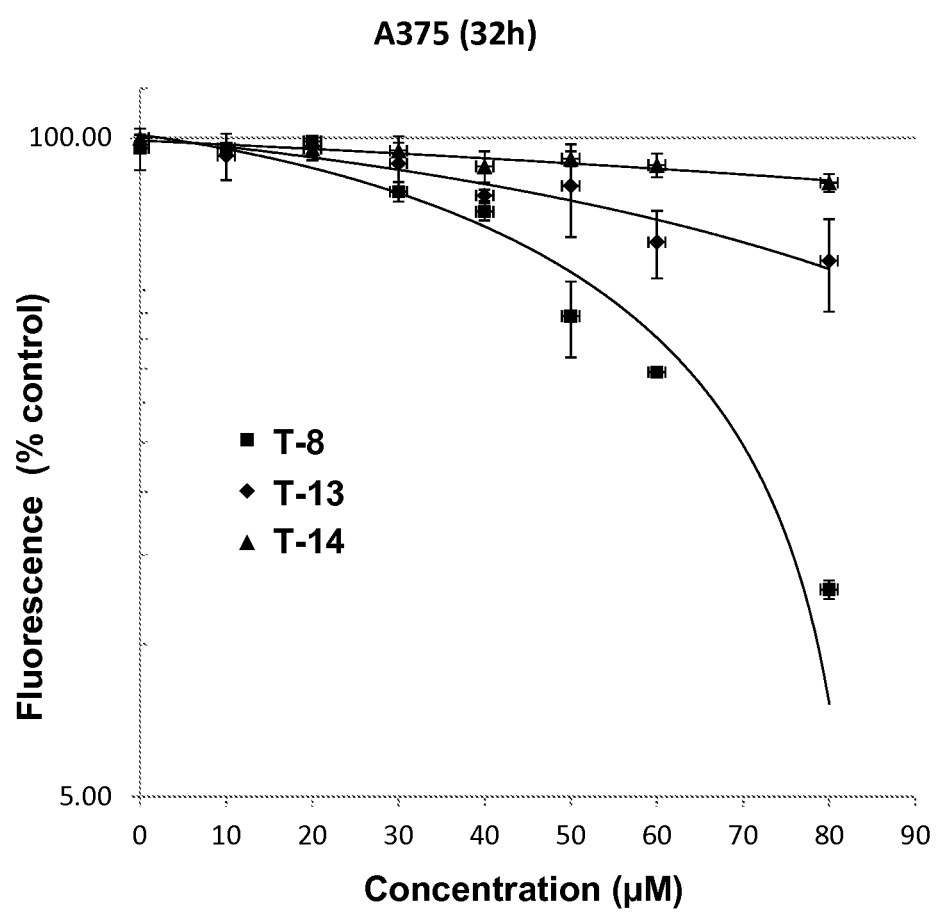

FIG. 8A displays the cytotoxicity of T-8, T-13, and T-14 in HeLa cells and FIG. 8B displays the cytotoxicity of T-8, T-13, and T-14 in A375 cells. For both cell types, T-8 appears to be most effective at reducing viability, followed by T-13, while T-14 shows the least efficacy.

Figure 9:
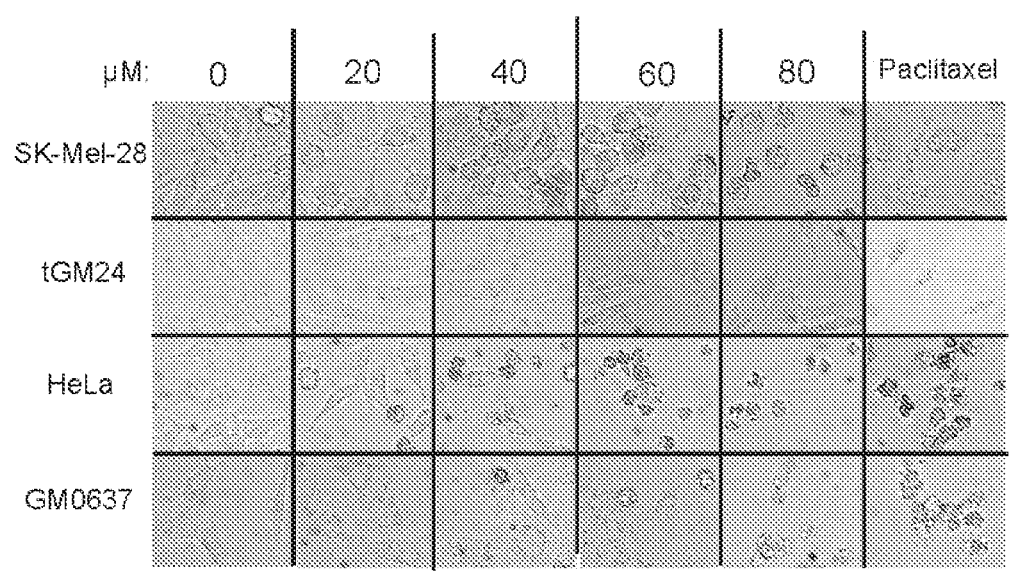
FIG. 9. Visual assessment of cytotoxicity of T-8 in paclitaxel sensitive and resistant cell lines. SK-MEL-28 (paclitaxel resistant human melanoma), tGM24 (telomerase immortalized human diploid skin fibroblasts), HeLa (paclitaxel sensitive human cervical carcinoma), and GM0637 (SV40-transformed human skin fibroblasts) were seeded in 24-well plates and exposed to the indicated concentrations of T-8 or 100 nM paclitaxel for 49 h.

FIG. 9 shows the visual assessment of cytotoxicity of T-8 in several cell lines including SK-MEL-28 (paclitaxel resistant human melanoma), tGM24 (telomerase immortalized human diploid skin fibroblasts), HeLa (paclitaxel sensitive human cervical carcinoma), and GM0637 (SV40-transformed human skin fibroblasts). Mitotic cells and apoptotic cells accumulated in SK-MEL-28, HeLa, and GM0637, but not in tGM24. Increase in cell number was less apparent in tGM24. These results demonstrate the selectivity of T-8 for carcinoma cells and transformed cells compared to normal diploid cells. The growth of normal diploid cells appeared to be inhibited, but cell death was not observed.

Figure 10:
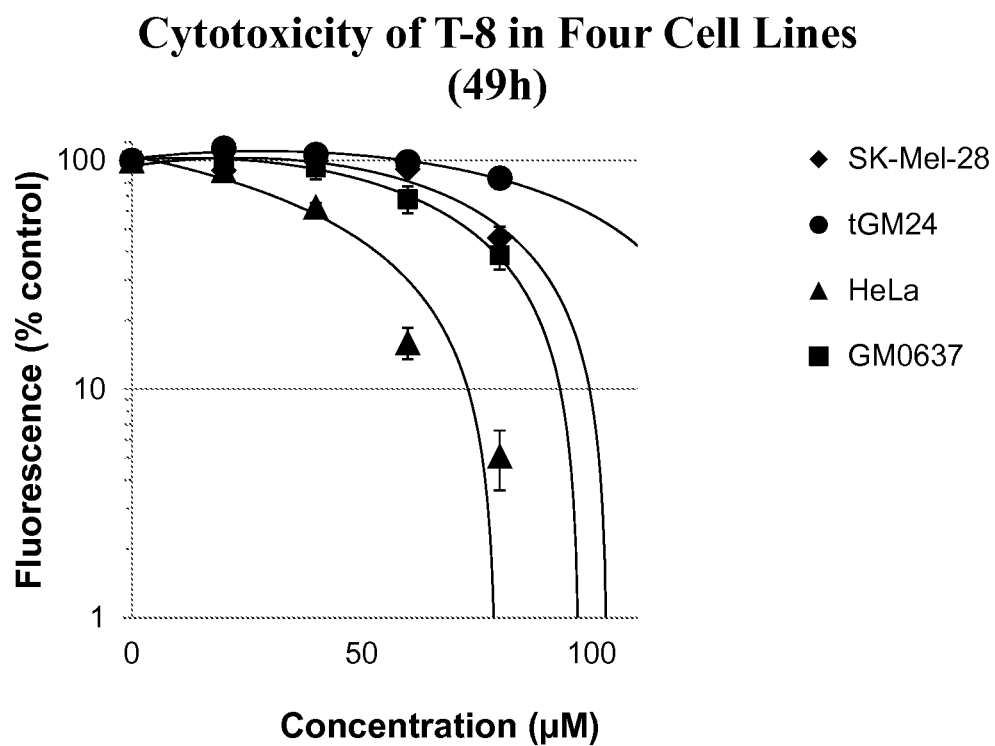
FIG. 10. Cytotoxicity of T-8 in paclitaxel sensitive and resistant cell lines assayed with Alamar Blue. SK-MEL-28, tGM24, HeLa, and GM0637 were seeded in 96-well plates and exposed to the indicated concentrations of T-8 for 32 h. Alamar Blue was added during the final 6 h of incubation and fluorescence was read on a plate reader. All values were corrected by the average of the blank (media only) wells, then normalized to the DMSO "zero" controls. A polynomial line of best fit has been included for each data set. All values beyond 80 μM are extrapolated from the polynomial line of best fit.

FIG. 10 shows the cytotoxicity of T-8 in paclitaxel sensitive and resistant cell lines assayed with Alamar Blue. T-8 appeared most effective in inducing cytotoxicity in HeLa cells. SK-MEL-28 and GM0637 indicated a moderate sensitivity. tGM24 cells appeared relatively resistant, which is consistent with the selective effect on carcinoma cells and transformed cells.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the specification, "a" or "an" may mean one or more. As used in the claims, when used in conjunction with the word "comprising," the words "a" or "an" may mean one or more than one. As used herein "another" may mean at least a second or more. As used in the specification, the phrases "such as" and "e.g." mean "for example, but not limited to" in that the list following "such as" or "e.g." provides some examples but is not necessarily a fully inclusive list.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

What is claimed is:

1. A method for treating a disease in an animal comprising administering a composition comprising a compound, to the animal wherein the disease is a cancer selected from the group consisting of basal cell carcinoma, thyroid cancer, squamous cell carcinoma, neuroblastoma, ovarian cancer, melanoma, renal cell carcinoma, hepatocellular carcinoma, cervical cancer, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, uterine cancer, and leukemias, and the compound is selected from a compound of Formula (II)

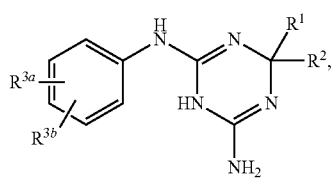
(II)

(II), salts of Formula (II), optical isomers of Formula (II), geometric isomers of Formula (II), salts of optical isomers of Formula (II), and salts of geometric isomers of Formula (II),
wherein
$R^1$ and $R^2$ are the same or different, are hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl, are each substituted or unsubstituted, are bonded together to form a cyclic ring, and if substituted, are substituted with hydroxyl, amine, amide, halogen, oxo, or nitro, and if $R^1$ and $R^2$ are bonded to form a cycloalkyl, one or more heteroatoms optionally replace one or more carbons in the cycloalkyl,
$R^{3a}$ is H, halogen, hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, and
$R^{3b}$ is H, halogen, hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro,
and
the compound is not

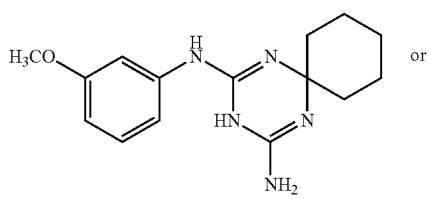 or

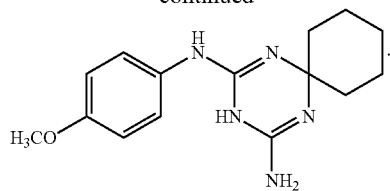

2. The method of claim 1, further comprising identifying an animal with the disease.

3. The method of claim 1, wherein the disease is a cancer selected from the group consisting of basal cell carcinoma, squamous cell carcinoma, ovarian cancer, melanoma, renal cell carcinoma, breast cancer, colon cancer, lung cancer, pancreatic cancer, chronic lymphocytic leukemia (CLL), acute lymphoblastic leukemia, cervical cancer, leukemias, prostate cancers, nasopharyngeal carcinoma, kidney cancer, rectal cancer, stomach cancer, and uterine cancer.

4. The method of claim 1, wherein the disease comprises a cancerous tumor.

5. The method of claim 1, wherein the disease is a cancer selected from the group consisting of ovarian cancer, melanoma, breast cancer, lung cancer, pancreatic cancer, and leukemias.

6. The method of claim 1, wherein the compound induces mitotic arrest.

7. The method of claim 1, wherein the compound induces mitotic catastrophe.

8. The method of claim 1, wherein the compound inhibits activity of APC/C.

9. The method of claim 1, wherein the compound inhibits licensing the pre-replication complexes.

10. The method of claim 1, wherein the animal is a mammal.

11. The method of claim 1, wherein the animal is a human.

12. The method of claim 1, wherein the administering is by an oral route or by a parenteral route.

13. The method of claim 1, wherein the composition comprises a racemic mixture of the compound.

14. The method of claim 1, wherein the composition comprises

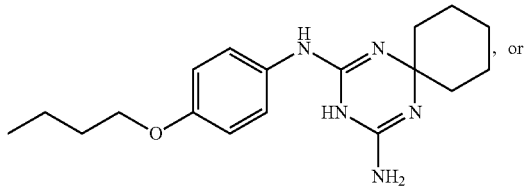
I-3
, or

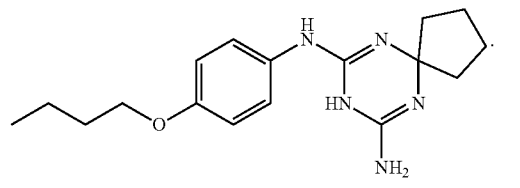
II-1

15. The method of claim 1, wherein $R^1$ and $R^2$ are bonded together to form a cycloalkyl optionally with one or more heteroatoms replacing one or more carbons in the cycloalkyl, optionally the cycloalkyl is fused to a substituted or unsubstituted cyclohexene, cyclohexadiene, benzene, cyclopentene, cyclopentadiene, furan, pyran, pyrrole, imidazole, pyrazole, pyridine, pyrazine, pyrimidine, or pyridazine, and if substituted, is substituted with hydroxyl, amine, amide, halogen, oxo, or nitro.

16. The method of claim 1, wherein $R^1$ and $R^2$ are bonded together to form a cycloalkyl optionally with one or more heteroatoms replacing one or more carbons in the cycloalkyl, wherein the cycloalkyl is cyclopropyl, cyclobutyl, cyclopentyl, cyclohexyl, cycloheptyl, cyclooctyl, or cyclononyl.

17. The method of claim 1, wherein $R^1$ and $R^2$ are bonded together to form cyclobutyl, cyclopentyl, cyclohexyl, cycloheptyl, or lactam.

18. The method of claim 1, wherein the disease is a cancer selected from the group consisting of ovarian cancer, melanoma, breast cancer, lung cancer, pancreatic cancer, chronic lymphocytic leukemia (CLL), acute lymphoblastic leukemia, cervical cancer, and leukemias.

19. The method of claim 1, wherein $R^1$ and $R^2$ are the same or different, are hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl are unsubstituted, are bonded, and if $R^1$ and $R^2$ are bonded together to form a cycloalkyl, no heteroatoms replace one or more carbons in the cycloalkyl; and $R^{3a}$ and $R^{3b}$ are the same or different, are unsubstituted, and are H, halogen, hydroxyl, methoxy, ethoxy, propoxy, butoxy, pentoxy, hexoxy, methyl, ethyl, propyl, butyl, pentyl, hexyl, or heptyl.

20. The method of claim 1, wherein if $R^1$ and $R^2$ are bonded together to form a cyclohexyl and one of $R^{3a}$ or $R^{3b}$ is a methoxy or an ethoxy, then the other of $R^{3a}$ or $R^{3b}$ is not H.

21. The method of claim 1, wherein if $R^1$ and $R^2$ are bonded together to form a cyclohexyl and one of $R^{3a}$ or $R^{3b}$ is a methoxy, then the other of $R^{3a}$ or $R^{3b}$ is not H.

22. The method of claim 1, wherein if one of $R^{3a}$ or $R^{3b}$ is a methoxy or an ethoxy, then the other of $R^{3a}$ or $R^{3b}$ is not H.

23. The method of claim 1, wherein if one of $R^{3a}$ or $R^{3b}$ is methoxy, then the other of $R^{3a}$ or $R^{3b}$ is not H.

24. The method of claim 1, wherein
$R^{3a}$ is H, halogen, hydroxyl, ethoxy, propoxy, butoxy, pentoxy, hexoxy, methyl, ethyl, propyl, butyl, pentyl, hexyl, or heptyl, which ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, and $R^{3b}$ is H, halogen, hydroxyl, ethoxy, propoxy, butoxy, pentoxy, hexoxy, methyl, ethyl, propyl, butyl, pentyl, hexyl, or heptyl, which ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro.

25. The method of claim 1, wherein
$R^{3a}$ is H, halogen, hydroxyl, propoxy, butoxy, pentoxy, hexoxy, methyl, ethyl, propyl, butyl, pentyl, hexyl, or heptyl, which propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, and $R^{3b}$ is H, halogen, hydroxyl, propoxy, butoxy, pentoxy, hexoxy, methyl, ethyl, propyl, butyl, pentyl, hexyl, or heptyl, which propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro.

26. The method of claim 1, wherein
(a) $R^1$ and $R^2$ are bonded together to form a cyclohexyl and
(i) $R^{3a}$ is halogen, hydroxyl, ethoxy, propoxy, butoxy, pentoxy, hexoxy, methyl, ethyl, propyl, butyl, pentyl, hexyl, or heptyl, which ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, and $R^{3b}$ is H, halogen, hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, (ii) $R^{3a}$ is H, halogen, hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, and $R^{3b}$ is halogen, hydroxyl, ethoxy, propoxy, butoxy, pentoxy, hexoxy, methyl, ethyl, propyl, butyl, pentyl, hexyl, or heptyl, which ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, or (iii) $R^{3a}$ is methoxy, which methoxy is substituted or unsubstituted, and if substituted, is substituted with hydroxyl, amine, amide, halogen, oxo, or nitro, and
$R^{3b}$ is methoxy, which methoxy is substituted or unsubstituted, and if substituted, is substituted with hydroxyl, amine, amide, halogen, oxo, or nitro, or (b) $R^1$ and $R^2$ are bonded together and do not form a cyclohexyl,
$R^{3a}$ is H, halogen, hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, and $R^{3b}$ is H, halogen, hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro.

27. The method of claim 1, wherein
(i) $R^{3a}$ is halogen, hydroxyl, ethoxy, propoxy, butoxy, pentoxy, hexoxy, methyl, ethyl, propyl, butyl, pentyl, hexyl, or heptyl, which ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, and $R^{3b}$ is H, halogen, hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, (ii) $R^{3a}$ is H, halogen, hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, and $R^{3b}$ is halogen, hydroxyl, ethoxy, propoxy, butoxy, pentoxy, hexoxy, methyl, ethyl, propyl, butyl, pentyl, hexyl, or heptyl, which ethoxy, propoxy, butoxy, pentoxy, hexoxy, methyl, ethyl, propyl, butyl, pentyl, hexyl, or heptyl is substituted or unsubstituted, and if substituted, is substituted with hydroxyl, amine, amide, halogen, oxo, or nitro, or (iii) $R^{3a}$ is methoxy, which methoxy is substituted or unsubstituted, and if substituted, is substituted with hydroxyl, amine, amide, halogen, oxo, or nitro, and $R^{3b}$ is methoxy, which methoxy is substituted or unsubstituted, and if substituted, is substituted with hydroxyl, amine, amide, halogen, oxo, or nitro.

28. The method of claim 1, wherein $R^1$ and $R^2$ are different, are hydroxyl, methoxy, ethoxy, propoxy, butoxy, pentoxy, hexoxy, methyl, ethyl, propyl, butyl, pentyl, hexyl, or heptyl, which methoxy, ethoxy, propoxy, butoxy, pentoxy, hexoxy, methyl, ethyl, propyl, butyl, pentyl, hexyl, or heptyl, are each substituted or unsubstituted, are bonded together to form a cyclic ring, and if substituted, are substituted with hydroxyl, amine, amide, halogen, oxo, or nitro, and if $R^1$ and $R^2$ are bonded to form a cycloalkyl, one or more heteroatoms optionally replace one or more carbons in the cycloalkyl, or $R^1$ and $R^2$ are the same, are hydroxyl, methoxy, ethoxy, propoxy, butoxy, pentoxy, hexoxy, ethyl, propyl, butyl, pentyl, hexyl, or heptyl, which methoxy, ethoxy, propoxy, butoxy, pentoxy, hexoxy, ethyl, propyl, butyl, pentyl, hexyl, or heptyl, are each substituted or unsubstituted, are bonded together to form a cyclic ring, and if substituted, are substituted with hydroxyl, amine, amide, halogen, oxo, or nitro, and if $R^1$ and $R^2$ are bonded to form a cycloalkyl, one or more heteroatoms optionally replace one or more carbons in the cycloalkyl.

29. The method of claim 1, wherein if $R^1$ and $R^2$ are the same, then $R^1$ and $R^2$ are not methyl.

* * * * *